US011185552B2

(12) United States Patent
Gupte

(10) Patent No.: US 11,185,552 B2
(45) Date of Patent: Nov. 30, 2021

(54) INHIBITORS OF GLUCOSE-6-PHOSPHATE DEHYDROGENASE FOR TREATING CARDIOVASCULAR AND PULMONARY CONDITIONS

(71) Applicant: ICHOR, LLC., Lake Success, NY (US)

(72) Inventor: Sachin A. Gupte, Fishkill, NY (US)

(73) Assignee: ICHOR, LLC, Lake Success, NY (US)

( * ) Notice: Subject to any disclaimer, the term of this patent is extended or adjusted under 35 U.S.C. 154(b) by 0 days.

(21) Appl. No.: 16/349,676

(22) PCT Filed: Nov. 15, 2017

(86) PCT No.: PCT/US2017/061741
§ 371 (c)(1),
(2) Date: May 14, 2019

(87) PCT Pub. No.: WO2018/093856
PCT Pub. Date: May 24, 2018

(65) Prior Publication Data
US 2019/0290659 A1   Sep. 26, 2019

Related U.S. Application Data

(60) Provisional application No. 62/422,929, filed on Nov. 16, 2016.

(51) Int. Cl.
| *A61K 31/5685* | (2006.01) |
| *A61P 9/10* | (2006.01) |
| *A61P 9/12* | (2006.01) |
| *A61P 11/00* | (2006.01) |
| *A61K 45/06* | (2006.01) |
| *G01N 33/50* | (2006.01) |
| *A61K 31/569* | (2006.01) |
| *G01N 33/52* | (2006.01) |

(52) U.S. Cl.
CPC ........ *A61K 31/5685* (2013.01); *A61K 31/569* (2013.01); *A61K 45/06* (2013.01); *A61P 9/10* (2018.01); *A61P 9/12* (2018.01); *A61P 11/00* (2018.01); *G01N 33/50* (2013.01); *G01N 33/52* (2013.01)

(58) Field of Classification Search
CPC .. A61K 31/5685; A61K 31/569; A61K 45/06; A61P 9/12; A61P 11/00; A61P 9/10; G01N 33/50; G01N 33/52
See application file for complete search history.

(56) References Cited

U.S. PATENT DOCUMENTS 7,456,161 B2 * 11/2008 Nyce .................. A61K 9/0073
514/178
2003/0044865 A1    3/2003 Fei et al.
2013/0102577 A1    4/2013 Kerr et al.

FOREIGN PATENT DOCUMENTS

WO    WO-2007/117084 A1    10/2007
WO    WO 2008089440 A2     7/2008
WO    WO 2012160006 A1     11/2012

OTHER PUBLICATIONS

Hamilton et al., J. Med. Chem. 2012, 55, 4431-4445. (Year: 2012).*
Chettimada et al., Am J Physiol Lung Cell Mol Physiol. Feb. 1, 2015; 308(3): L287-L300 (Year: 2015).*
Shin et al., Heart Fail Clin. Apr. 2010; 6(2): 215-222. (Year: 2010).*
Handoko et al., Eur Respir Rev 2010; 19: 115, 72-82. (Year: 2010).*
Bale et al., Sympsium Report, 2013 (Year: 2013).*
Extended European Search Report in corresponding European Application No. EP 17 87 2327, dated May 25, 2020.
Gupte Sachin A, "Glucose-6-phosphate dehydrogenase: a novel therapeutic target in cardiovascular diseases", Current Opinion in Investigational Drugs, Pharmapress, US, Aug. 31, 2008, vol. 9, No. 9, pp. 993-1000.
Sukrutha Chettimada et al, "Hypoxia-induced glucose-6-phosphate dehydrogenase overexpression and -activation in pulmonary artery smooth muscle cells: implication in pulmonary hypertension", American Journal of Physiology—Lung Cellular and Molecular Physiology, US, Feb. 1, 2015, vol. 308, No. 3, pp. 287-300.
Gordon G B et al, "Reduction of Atherosclerosis by Administration of Dehydroepiandrosterone. A Study in the Hypercholesterolemic New Zealand White Rabbit With Aortic Intimal Injury", Journal of Clinical Investigation, B M J Group, GB, Aug. 1, 1988, vol. 82, No. 2, pp. 712-720.
Sukrutha Chettimada et al, "Vascular smooth muscle cell contractile protein expression is increased through protein kinase G-dependent and -independent pathways by glucose-6-phosphate dehydrogenase inhibition and deficiency", American Journal of Physiology: Heart and Circulatory Physiology, US, Oct. 1, 2016, vol. 311, No. 4, pp. H904-H912.
Sabrina Serpillon et al, "Superoxide production by NAD(P)H oxidase and mitochondria is increased in genetically obese and hyperglycemic rat heart and aorta before the development of cardiac dysfunction. The role of glucose-6-phosphate dehydrogenase-derived NADPH", American Journal of Physiology—Heart and Circulatory Physiology, United States, Jul. 1, 2009, pp. 153-162.
International Search Report and Written Opinion in corresponding PCT Application No. PCT/US2017/061741, dated Mar. 6, 2018.
Hamilton et al., "Novel Steriod Inhibitors of Glucose 6-Phosphate Dehydrogenase," J. Med. Chem. 2012, vol. 55, pp. 4431-4445, entire document, especially; p. 4433, Scheme 3, Compound 17b.
Dehydroepiandrosterone—C19H28O2—PubChem-CID 5881, Create Date: Sep. 16, 2004, pp. 1-44; p. 4, Fig.
International Preliminary Report on Patentability in corresponding PCT Application No. PCT/US2017/061741, dated May 31, 2019.
Japanese Office Action in corresponding Japanese Application No. 2019-547229, dated Sep. 23, 2021 and English translation.

* cited by examiner

*Primary Examiner* — Jean P Cornet
(74) *Attorney, Agent, or Firm* — Leason Ellis LLP

(57) ABSTRACT

The present disclosure provides for methods of treating or preventing a cardiovascular disorder and/or a related pulmonary disorder in a subject. In certain embodiments, the method comprises administering a therapeutically effective amount of an inhibitor of Glucose-6-phosphate dehydrogenase (G6PD), or a pharmaceutically acceptable salt, non-salt amorphous form, solvate, poly-morph, tautomer or prodrug thereof.

4 Claims, 9 Drawing Sheets

| Condition | Body weight (gm) | | Hematocrit (%) |
|---|---|---|---|
| | 0 wk | 5 wk | |
| Control | 23.5+/-1.8 | 26.2+/-1.1 | 44.6+/-1.3 |
| PH | 21.0+/-0.4 | 24.2+/-1.2 | 49.7+/-1.0 |
| PH+PD2124 (1.3 mg/kg s.c.) | 23.5+/-3.2 | 22.8+/-1.8 | 39.3+/-1.5 |

Mean+/-SEM

Fig. 2

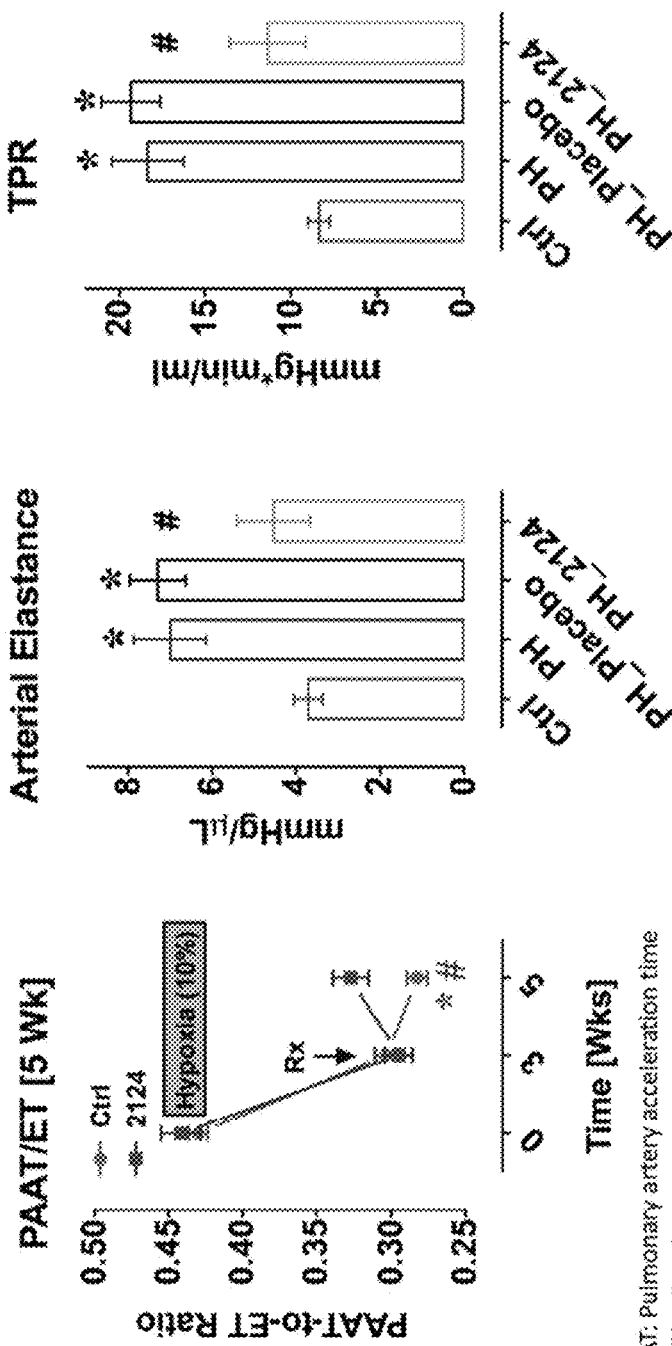

INHIBITORS OF GLUCOSE-6-PHOSPHATE DEHYDROGENASE FOR TREATING CARDIOVASCULAR AND PULMONARY CONDITIONS

CROSS REFERENCE TO RELATED APPLICATION

This application is a U.S. National Phase Application under 35 U.S.C. § 371 of International Patent Application No. PCT/US2017/061741, filed Nov. 15, 2017, and claims the benefit of priority under 35 U.S.C. Section 119(e) of U.S. Application No. 62/422,929, filed Nov. 16, 2016, all of which are incorporated by reference in their entireties. The International Application was published on May 24, 2018 as International Publication No. WO 2018/093856 A1.

FIELD OF THE INVENTION

The present invention relates to treating or preventing cardiovascular diseases using an inhibitor of glucose-6-phosphate dehydrogenase (G6PD).

BACKGROUND

Cardiovascular diseases are among the leading causes of mortality and morbidity worldwide with ever-increasing prevalence. Cardiovascular diseases include numerous conditions that affect the heart, heart valves, blood, and blood vessels (arteries, capillaries, and veins) of the body. The causes of cardiovascular disease are diverse but atherosclerosis and/or hypertension are the most common. Risk factors include elevated plasma total or LDL cholesterol, elevated triglycerides, low HDL cholesterol, e.g. hyperlipidemia, hypercholesterolemia, or hypoalphalipoproteinemia, and increased inflammatory markers such as C-reactive protein and fibrinogen.

Major cardiovascular diseases including stroke, atherosclerosis, and hypertension, as well as orphan diseases such as pulmonary hypertension, angiosarcoma, hemangiosarcoma, and hypertrophic cardiomyopathies, are incurable. In addition, medical therapies to treat congestive heart failure and pulmonary hypertension-associated heart failure are inadequate.

Pulmonary hypertension presents an increase of blood pressure in the pulmonary artery, pulmonary vein, or pulmonary capillaries, together known as the lung vasculature, leading to shortness of breath, dizziness, fainting, leg swelling and other symptoms. Pulmonary circulation is a low resistance, low pressure, and high compliant vascular bed. In pulmonary hypertension, the pressure in the pulmonary artery rises above normal levels. Normally, pulmonary artery pressure is maintained around 20-25 mmHg Pulmonary hypertension is defined when the pressures increase to more than 30 mmHg Pulmonary hypertension is a major cause of morbidity and mortality in patients with several different clinical conditions. Pulmonary hypertension is a progressive disease and the pathophysiology of pulmonary hypertension is heterogeneous. Severe pulmonary hypertension remains debilitating and deadly. Pulmonary hypertension is divided into five groups with diverse etiologies. In all forms of pulmonary hypertension, pulmonary artery pressure increases mainly because of increased pulmonary constriction/resistance and narrowing or remodeling of pulmonary artery and veins. One cause of pulmonary hypertension is alveolar hypoxia, which results from localized inadequate ventilation of well-perfused alveoli or from a generalized decrease in alveolar ventilation. Pulmonary hypertension is also a vascular permeability related disease. Current therapies are inadequate to reverse the complex pulmonary vascular remodeling and reduce pulmonary vascular resistance. Pulmonary hypertension has been historically chronic and incurable with a poor survival rate. Treatment of pulmonary hypertension usually involves continuous use of oxygen. Pulmonary vasodilators (e.g., hydralazine, calcium blockers, nitrous oxide, prostacyclin) have not proven effective, and lung transplant is often required for patients who do not respond to therapy.

Arteriosclerosis, which is induced and progressed by various risk factors, causes thickening of the arterial lumen to interrupt blood flow, resulting in a cardiovascular disease such as aortic aneurysm, angina, myocardial infarction, or cerebral infarction.

Cardiac hypertrophy is an adaptive response of the heart cells to elevated levels of biomechanical stress imposed by a variety of extrinsic and intrinsic stimuli including pressure or volume overload, familial/genetic cardiomyopathies, or loss of contractile mass from preceding infarction (Frey et al. (2004) Circulation 109:1580-1589; Frey et al. (2003) Annu. Rev. Physiol. 65:45-79; Yoshida et al. (1986) J. Cardiogr. 16:399-406). If sustained, hypertrophy often becomes pathological, accompanied by significant risk of arrhythmia, progression to heart failure, and sudden death (Frey et al. (2004), supra; Levy et al. (1990) N. Engl. J. Med. 322:1561-1566; Koren et al. (1991) Ann. Intern. Med. 114:345-352). At the molecular level, pathological hypertrophy is associated with re-induction of the so-called fetal gene program in which the fetal isoforms of genes responsible for regulating cardiac contractility and calcium handling (e.g. .beta.-MHC) are upregulated (Frey et al. (2004), supra; Frey et al. (2003), supra); Olson (2004) Nat. Med. 10:467-474; Iemitsu et al. (2001) Am. J. Physiol. Regul. Integr. Comp. Physiol. 281:R2029-2036). At the cellular level, the main characteristics of ventricular hypertrophic growth are enhanced protein synthesis and an increase in size of cardiomyocytes (Frey et al. (2004), supra; Frey et al. (2003), supra). As pathologic hypertrophy progresses, these changes in molecular and cellular phenotypes are accompanied by an increase in apoptosis, fibrosis, chamber dilation, and decreased systolic function (Frey et al. (2004), supra).

Heart failure is associated with high morbidity as well as significant mortality. The clinical syndrome of heart failure is the result of heterogeneous myocardial or vascular diseases, and is defined by insufficiency to maintain blood circulation throughout the body. Despite significant advances in the clinical management of heart failure, conventional therapies are ultimately ineffective in many patients who progress to advanced heart failure. In these cases, implantation of left ventricular assist devices (LVAD) and/or heart transplantation can be the only viable options.

In view of the foregoing, there is a need to develop effective treatments for various cardiovascular disorders. In this disclosure, novel therapies to treat cardiovascular disorders, such as pulmonary hypertension, pulmonary hypertension-associated heart failure, atrial fibrillation or arrhythmia, and cardiomyopathies are described.

SUMMARY OF THE INVENTION

In certain embodiments, the present invention relates to a method for treating or preventing a cardiovascular disorder and/or a pulmonary disorder in a subject in need thereof, comprising administering to the subject a therapeutically effective amount of an inhibitor of Glucose-6-phosphate dehydrogenase (G6PD), or a pharmaceutically acceptable salt, solvate, poly-morph, tautomer or prodrug thereof.

In certain embodiments, the inhibitor comprises a compound having the formula of Formula I, Formula II, Formula III, Formula IV, Formula V, Formula IV, Formula VII, or Formula VIII, or any combination thereof.

In additional embodiments, the inhibitor comprises N-[(3β,5α)-20-Oxopregnan-3-yl] methanesulfonamide; N-ethyl-N'-[(3β, 5α)-17-oxoandrostan-3-yl]urea; (3β,5α)-3,21-Dihydroxypregnan-20-one, or any combination thereof.

In additional embodiments, the cardiovascular disorder comprises pulmonary hypertension, pulmonary hypertension-associated heart failure, congestive heart failure, cardiomyopathies, arrhythmia including atrial fibrillation, hypertension, stroke, medial hypertrophy, acute neointimal formation following iatrogenic interventions, atherosclerosis, or combinations thereof.

In further embodiments, the cardiovascular disorder and/or pulmonary disorder comprises angiosarcoma, hemangioscarcoma, Timothy Syndrome, hypertrophic cardiomyopathy, or combinations thereof. In additional embodiments, the cardiovascular disorder and/or pulmonary disorder comprises any of the groups of pulmonary hypertension 1-5, or combinations thereof. In additional embodiments, the disorder comprises scleroderma, categorized as pulmonary hypertension group I.

In certain embodiments, the method further comprises treating the subject with a diuretic, a vasodilator, an inotropic agent, an angiotensin converting enzyme (ACE) inhibitor, a beta blocker, a neurohumoral blocker, an aldosterone antagonist, histone deactylase inhibitors, erythropoietin, or combinations thereof.

In certain embodiments, the method further comprises treating the subject with a medical device and/or surgery. In certain embodiments, the medical device comprises a bi-ventricular pacemaker, an implantable cardioverter-defibrillator (ICD), a ventricular assist device (VAD), a left ventricular assist device (LVAD), a cardiac resynchronization therapy (CRT), or combinations thereof.

In certain embodiments, the present invention relates to use of a compound having the formula of Formula I, Formula II, Formula III, Formula IV, Formula V, Formula IV, Formula VII, or Formula VIII, or any combination thereof, or a pharmaceutically acceptable salt (crystal and/or amorphous), non-salt amorphous form, solvate, poly-morph, tautomer or prodrug thereof in the preparation of a pharmaceutical composition for treating or preventing a cardiovascular disorder and/or a pulmonary disorder in a subject in need thereof.

BRIEF DESCRIPTION OF THE DRAWINGS

FIG. 2 is a table showing results for mice exposed to hypoxia (10% O2) or to ambient atmosphere (21% $O_2$) for 5 wk. These mice developed pulmonary hypertension (PH group). Mice were treated with PD2124 (Compound 34) s.c. for 1 wk. Body weight and hematocrit was measured.

FIG. 3A) and smooth muscle myosin heavy chain (MHY11; FIG. 3B) expression was increased by PD2958 (10 microM) and PD2124 (1 microM).

FIGS. 8A-8C are graphs showing results for mice that were divided into four groups and treated under the following conditions: control (ctrl) exposed to ambient atmosphere (21% $O_2$); pulmonary hypertension exposed to 10% $O_2$ (PH); PH treated with inactive G6PD inhibitor (PH_Placebo); and PH treated with active G6PD inhibitor (PH_2124) for 5 wk. Placebo and 2124 were injected S.C. (1.3 mg/Kg) for 1 wk from wk 4 to wk 5. G6PD inhibitor 2124 reduced and reversed pulmonary resistance determined as PAAT-to-ET ratio (FIG. 8A), arterial elastance (FIG. 8B), and TPR (FIG. 8C).

DETAILED DESCRIPTION

Figure 1:
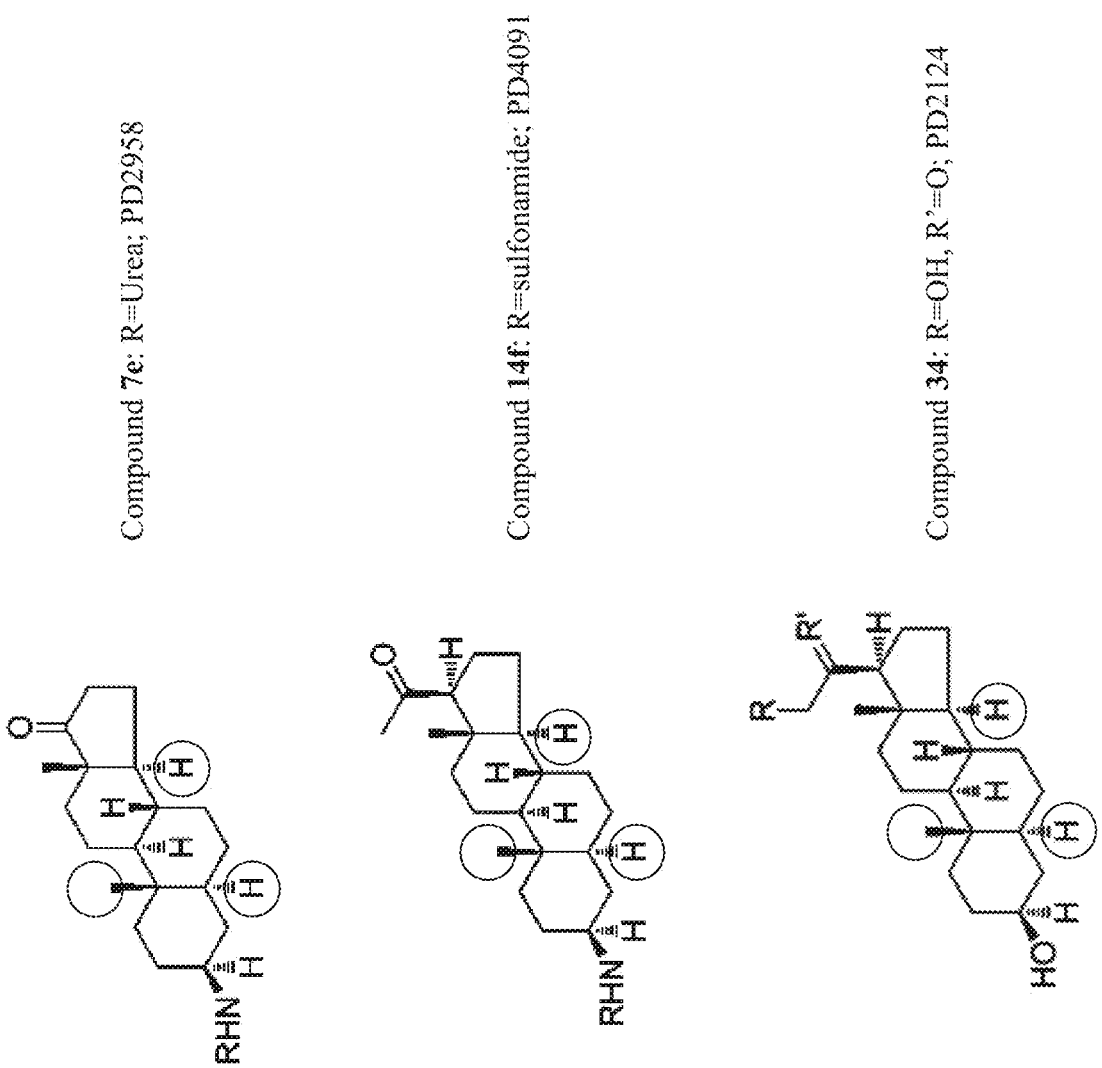
FIG. 1 shows the structures of Compound 7e, 14f and 34. Circles indicate hydrogen residue replacement with CH3 or O inactivates the drug from inhibiting G6PD and lose their cardiovascular actions.

As described herein we provide methods as well as one or more agents/compounds that inhibit G6PD for the treatment, prophylaxis or alleviation of cardiovascular conditions described herein, or related pulmonary conditions, or predisposition to such a condition.

The present disclosure provides for methods of treating or preventing a cardiovascular disorder and/or a related pulmonary disorder in a subject. In the method, a therapeutically effective amount of an inhibitor of Glucose-6-phosphate dehydrogenase (G6PD) is administered. The inhibitor may be a compound having the formula according to Formula I, Formula II, Formula III, Formula IV, Formula V, Formula IV, Formula VII, or Formula VIII.

In certain embodiments, the present composition comprises one or more of the following compounds: N-[(3β,5α)-20-Oxopregnan-3-yl] methanesulfonamide; N-ethyl-N'-[(3β,5α)-17-oxoandrostan-3-yl]urea; and (3β,5α)-3,21-Dihydroxypregnan-20-one. Table 1 lists the structures of exemplary compounds of the present disclosure.

In certain embodiments, the present agent/composition is specifically administered to lung or cardiac cells, to inhibit gene function and prevent one or more of the symptoms and processes associated with the progression of cardiovascular or pulmonary conditions. Such treatment may also be useful in treating patients who already exhibit cardiovascular or

TABLE 1

| Compound | Chemical Name | Structure | Synthesis |
|---|---|---|---|
| PD109 (109) | 5-Androsten-3-beta-hydroxy-17-one (Dehydroepiandrosterone) | 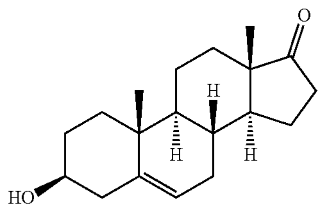 | (Commercially available, CAS Number 53-43-0) |
| PD2124 (2124); Compound 34 | (3β,5α)-3,21-Dihydroxypregnan-20-one | R = OH, R' = O | Example 2 |
| PD2958 (2958); Compound 7e | N-Ethyl-N'-[(3β,5α)-17-oxoandrostan-3-yl]urea | R = Urea | Example 2 |
| PD4091 (4091); Compound 14f | N-[(3β,5α)-20-Oxopregnan-3-yl]methanesulfonamide | R = sulfonamide | Example 2 |

In yet additional embodiments, the invention relates to a pharmaceutical composition comprising a pharmaceutically effective amount of a compound of Formula I, Formula II, Formula III, Formula IV, Formula V, Formula IV, Formula VII, or Formula VIII, or a pharmaceutically acceptable salt (crystal and/or amorphous), non-salt amorphous form, solvate, poly-morph, tautomer or prodrug thereof. In certain embodiments, the compound further comprises a pharmaceutically acceptable carrier, diluent, excipient and/or adjuvant.

pulmonary conditions, to reverse or alleviate one or more of the disease processes. Additionally, approaches utilizing one or more additional inhibitors including an inhibitor of protein kinase G and blocker of endothelin A or B receptor or any combination of these, are also expected to be useful for treating certain conditions.

In an embodiment, "patient" or "subject" refers to mammals and includes human and veterinary subjects, including avians. In an embodiment, the subject is mammalian.

Glucose-6-Phosphate Dehydrogenase (G6PD)

Glucose-6-phosphate dehydrogenase (G6PD) generates nicotinamide adenine dinucleotide phosphate reduced (NADPH), a key cofactor for various redox-sensitive enzymes like: NADPH oxidases, glutathione/thioredoxin reductases, and other reductive and anabolic reactions in the cell (Gupte and Wolin (2012): Hypertension; 60:269-275). We have shown that G6PD is involved in regulation of coronary and pulmonary artery contraction and relaxation (Ata et al (2011): Am J Physiol Heart Circ Physiol; 300:H2054-H2063), and pulmonary artery SMC phenotype (Chettimada et al (2012): Am J Physiol Lung Cell Mol Physiol; 303:L64-L74). Glucose-6-phosphate dehydrogenase has been shown to be associated with progressive pulmonary artery remodeling in pulmonary hypertension.

Glycolysis, glucose flux through the PPP, and the activity of NADPH producing isocitrate dehydrogenase-1 and -2 are increased in pulmonary artery of idiopathic- and heritable-pulmonary hypertension patients, and in endothelial cells and fibroblasts from idiopathic pulmonary hypertension patients. G6PD expression and activity are increased in: (a) endothelin-1 treated pulmonary artery smooth muscle cells from pulmonary hypertension patients; (b) hypoxic cultured rat pulmonary artery smooth muscle cells; and (c) lungs of pulmonary hypertensive rat models. G6PD is a major supplier of NADPH (60% by G6PD+40% by isocitrate dehydrogenase) for: anabolic reactions and superoxide production from NADPH oxidases in the cell. Excess NADPH generation contributes to pathogenic "reductive stress" in cardiovascular system.

G6PD-derived NADPH plays a key role in stimulating proliferation and inhibiting apoptosis of cells (Buchakjian and Kornbluth (2010): Nat Rev Mol Cell Biol; 11:715-727). Ectopic expression of G6PD increases rat PASMC proliferation (Chettimada et al (2015): Am J Physiol Lung Cell Mol Physiol; 308:L287-L300) and contributes to the HIF1α-induced endothelial growth (Leopold et al (2003): J Biol Chem; 278:32100-32106). Additionally, our findings suggest that hyper-activation of G6PD in $CD133^+$ progenitor cells promote their self-renewal (Chettimada et al (2014): Am J Physiol Lung Cell Mol Physiol; 307:L545-L556). $CD133^+$ cells potentially participate in the PA remodeling process in PAH (Asosingh et al (2008): Am J Pathol; 172:615-627). Conversely, inhibition of G6PD increases the rate of apoptosis of *X laevis* oocytes, HEK293 cells, esophageal squamous cell carcinoma, and melanoma cells (Bouchier-Hayes et al (2009): Mol Cell; 35:830-840; Nutt et al (2005): Cell; 35:89-103; Wang et al (2016): Tumout Biol; 37:781-789; Cai et al (2015): Am J Cancer Res; 5:1610-1620). In PH, the PASMC and endothelial cell proliferation is accompanied by decreased expression of pro-apoptotic genes (Bull et al (2007): Proc Am Thorac Soc; 4:117-120). Therefore, altogether these findings allude stimulation of G6PD activity by endothelin-1 or by hypoxia likely inhibits apoptosis and promotes proliferation of PASMC, and contributes to progressive PA remodeling and to the pathogenesis of HPH and PAH.

G6PD deficiency is common in humans, and several point mutations have been found in this enzyme in different ethnic groups around the world. Epidemiological studies suggest that individuals who harbor a Mediterranean-type non-synonymous mutation [single nucleotide polymorphism in exon 6: dbSNP rs5030868] have 80% less G6PD activity as compared to normal individuals and are less likely to have cardiovascular diseases (Gupte (2008): Curr Opin Investig Drugs9:993-1000), including sickle cell anemia-associated PH.

Illustrative nucleotide sequences encoding the amino acid sequences of human G6PD are known and published, e.g., in GenBank Accession Nos. NM_000402, AH003054.2 etc. In some embodiments, the level of G6PD is decreased in a cardiac and/or lung cells.

In certain embodiments, treatment may be targeted to, or specific to, diseased cells. The expression of G6PD may be specifically decreased only in diseased cells (i.e., those cells which are predisposed to the cardiovascular condition and/or related pulmonary condition, or exhibiting cardiovascular condition and/or related pulmonary condition already), and not substantially in other non-diseased cells. In these methods, expression of G6PD may not be substantially reduced in other cells, i.e., cells which are non-diseased cells. Thus, in such embodiments, the level of G6PD remains substantially the same or similar in non-diseased cells in the course of or following treatment.

Cell specific reduction of G6PD levels and/or activity may be achieved by targeted administration, i.e., applying the treatment only to the targeted cells and not other cells. However, in other embodiments, down-regulation of G6PD expression in other cells (e.g., a portion of non-diseased cells, and not substantially in other cell or tissue types) is employed.

The methods and compositions described here may reduce the level and/or activity of G6PD, G6PD polynucleotides, G6PD nucleotides and G6PD nucleic acids, as well as variants, homologues, derivatives and fragments of any of these. The inhibitors targeting G6PD may also be used for the methods of treatment or prophylaxis described.

The terms "G6PD polynucleotide", "G6PD nucleotide" and "G6PD nucleic acid," "G6PD nucleic acid" may be used interchangeably, and should be understood to specifically include both cDNA and genomic G6PD sequences. These terms are also intended to include a nucleic acid sequence capable of encoding a G6PD polypeptide and/or a fragment, derivative, homologue or variant of this.

By "down-regulation" or "reduction" is meant any negative effect on the condition being studied; this may be total or partial. Thus, where the level or activity of a protein is being detected, the present agent is capable of reducing, ameliorating, or abolishing the level or activity of the protein. The down-regulation of the level or activity of the protein achieved by the present agent may be at least 10%, such as at least 20%, at least 30%, at least 40%, at least 50%, at least 60%, at least 70%, at least 80%, at least 90% or more compared to the level or activity of the protein in the absence of the present agent.

The term "compound" refers to a chemical compound (naturally occurring or synthesized), such as a biological macromolecule (e.g., nucleic acid, protein, non-peptide, or organic molecule), or an extract made from biological materials such as bacteria, plants, fungi, or animal (particularly mammalian) cells or tissues, or even an inorganic element or molecule. The compound may be an antibody.

In some embodiments, the anti-G6PD agent is provided as an injectable or intravenenous composition and administered accordingly. The dosage of the anti-G6PD agent inhibitor may be between about 5 mg/kg/2 weeks to about 10 mg/kg/2 weeks. The anti-G6PD agent inhibitor may be provided in a dosage of between 10-300 mg/day, such as at least 30 mg/day, less than 200 mg/day or between 30 mg/day to 200 mg/day.

Inhibitors of G6PD

The present disclosure provides methods of treating or preventing a cardiovascular disorder and/or a related pulmonary disorder in a subject by administering one or more compounds as described herein. In one embodiment, an androstane-derivative is used in the present method. In another embodiment, a preganane-derivative is used in the present method. In certain embodiments, the steroid inhibition of G6PD has been substantially developed; the 3β-alcohol can be replaced with 3β-H-bond donors such as sulfamide, sulfonamide, urea, and carbamate. In certain embodiments, improved potency was achieved by replacing the androstane nucleus with a pregnane nucleus, provided a ketone at C-20 is present. In certain embodiments, for pregnan-20-ones a 21-hydroxyl group is incorporated. *J. Medicinal Chemistry* 2012; 55:4431-4445.

In certain embodiments, the present compound has an IC50 in inhibiting G6PD activity ranging from about 0.1 µM to about 500 µM, from about 0.5 µM to about 200 µM, from about 1 µM to about 100 µM, from about 1 µM to about 50 µM, from about 1 µM to about 30 µM, or from about 1 µM to about 10 µM. In certain embodiments, the present compound displays at least 10 fold, at least 20 fold, at least 30 fold, at least 40 fold, at least 50 fold, at least 60 fold, at least 70 fold, at least 80 fold, at least 90 fold, at least 100 fold, at least 150 fold, at least 180 fold, or at least 200 fold, efficacy to inhibit G6PD activity in vitro and in vivo than dehydroepiandrosterone or epiandrosterone.

In accordance with the present invention, there is provided compounds of Formula I or Formula II, and methods for treating a cardiovascular disorder and/or a related pulmonary disorder in a patient, comprising administering to the patient any one of the compounds having Formula I or Formula II:

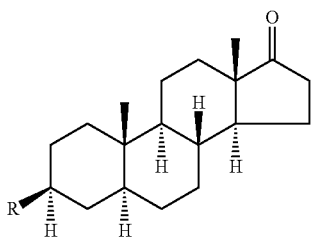

R = urea, carbamate,
sulfonamide, sulfamide

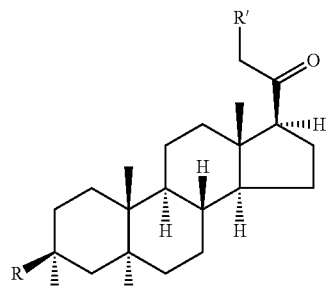

R = sulfonamide, sulfamide
R' = H, OH

In Formula I, R is urea, carbamate, sulfonamide or sulfamide.
In Formula II, R is sulfonamide or sulfamide; R' is H or OH.

In accordance with the present invention, there is provided compounds of Formula III or Formula IV, or V and methods for treating a cardiovascular disorder and/or a related pulmonary disorder in a patient, comprising administering to the patient any one of the compounds having Formula III, Formula IV or Formula V:

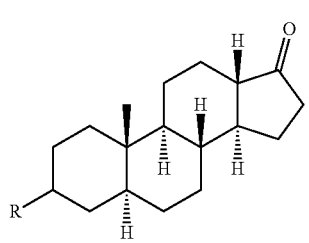

Wherein:
R is $R^1$NH and OH;
R1 is selected from H and moieties, NHacyl, $CONHR^2$, $CONR^3R^4$, $CO_2R^2$, $SO_2R^2$, $SO_2R^5$ and $SO_2NH_2$;
$R^2$ is straight and branched alkyl of 1 to 6 carbon atoms;
$R^3$ and $R^4$ are independently selected from H and straight and branched alkyl of 1 to 6 carbon atoms;
$R^5$ is phenyl optionally substituted with 1 or 2 substituents selected from fluorine, chlorine, and straight and branched alkyl of 1 to 6 carbon atoms.

The compounds of Class/Formula III may be obtained as inorganic or organic pharmaceutically acceptable salts using methods known to those skilled in the art (Richard C. Larock, Comprehensive Organic Transformations, VCH Publishers, 411-415, 1989). It is well known to one skilled in the art that an appropriate salt which include but not limited to inorganic salts which may be sodium, calcium, potassium or magnesium and the like or equivalent thereof or hydrochloric, hydrobromic, hydroiodic, phosphoric, nitric or sulfate and the like.

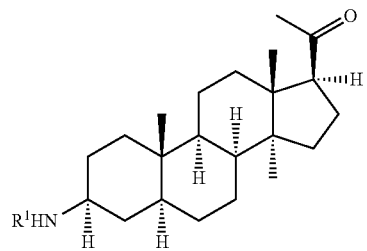

Where:
$R^1$ is selected from H and moieties, NHacyl, $CONHR^2$, $CONR^3R^4$, $CO_2R^2$, $SO_2R^2$, $SO_2R^5$ and $SO_2NH_2$;
$R^2$ is straight and branched alkyl of 1 to 6 carbon atoms;
$R^3$ and $R^4$ are independently selected from H and straight and branched alkyl of 1 to 6 carbon atoms;
$R^5$ is phenyl optionally substituted with 1 or 2 substituents selected from fluorine, chlorine, and straight and branched alkyl of 1 to 6 carbon atoms. The compounds of Class/Formula IV may be obtained as inorganic or organic pharmaceutically acceptable salts using methods known to those skilled in the art (Richard C. Larock, Comprehensive Organic Transformations, VCH Publishers, 411-415, 1989). It is well known to one skilled in the art that an appropriate salt which include but not limited to inorganic salts which may be sodium, calcium, potassium or magnesium and the like or equivalent thereof or hydrochloric, hydrobromic, hydroiodic, phosphoric, nitric or sulfate and the like.

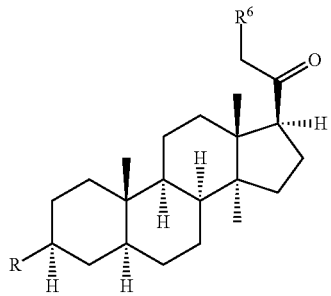

Formula V

Wherein:

R is R$^1$NH and OH;

R$^1$ is selected from H and moieties, NHacyl, CONHR$^2$, CONR$^3$R$^4$, CO$_2$R$^2$, SO$_2$R$^2$, SO$_2$R$^5$ and SO$_2$NH$_2$;

R$^2$ is straight and branched alkyl of 1 to 6 carbon atoms;

R$^3$ and R$^4$ are independently selected from H and straight and branched alkyl of 1 to 6 carbon atoms;

R$^5$ is phenyl optionally substituted with 1 or 2 substituents selected from fluorine, chlorine, and straight and branched alkyl of 1 to 6 carbon atoms;

R$^6$ is H or OH.

The compounds of Class/Formula V may be obtained as inorganic or organic pharmaceutically acceptable salts using methods known to those skilled in the art (Richard C. Larock, Comprehensive Organic Transformations, VCH Publishers, 411-415, 1989). It is well known to one skilled in the art that an appropriate salt which include but not limited to inorganic salts which may be sodium, calcium, potassium or magnesium and the like or equivalent thereof or hydrochloric, hydrobromic, hydroiodic, phosphoric, nitric or sulfate and the like.

In certain embodiments, the present composition comprises compounds of Formula VI, Formula VII, or Formula VIII. In certain embodiments, the present composition comprises one or more of the following compounds: N-[(3β,5α)-20-Oxopregnan-3-yl] methanesulfonamide (Formula VI, R=sulfonamide, also called "compound 14f" herein); N-ethyl-N-[(3β,5α)-17-oxoandrostan-3-yl]urea (Formula VII, R=Urea, also called "compound 7e" herein); or (3β,5α)-3,21-Dihydroxypregnan-20-one (Formula VIII, R=OH; R'=O; also called "compound 34" herein).

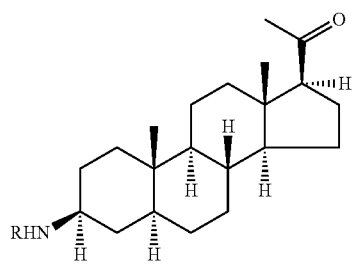

VI

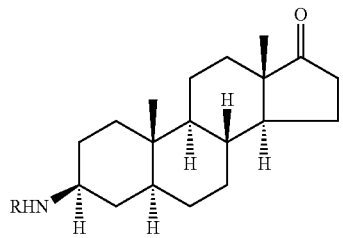

VII

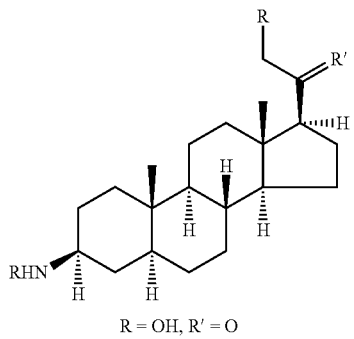

VIII

R = OH, R' = O

The compounds used in the methods of the present invention include all hydrates, solvates, and complexes of the compounds used by this invention. If a chiral center or another form of an isomeric center is present in a compound of the present invention, all forms of such isomer or isomers, including enantiomers and diastereomers, are intended to be covered herein. Compounds containing a chiral center may be used as a racemic mixture, an enantiomerically enriched mixture, or the racemic mixture may be separated using well-known techniques and an individual enantiomer may be used alone. The compounds described in the present invention are in racemic form or as individual enantiomers. The enantiomers can be separated using known techniques, such as those described in Pure and Applied Chemistry 69, 1469-1474, (1997) IUPAC. In cases in which compounds have unsaturated carbon-carbon double bonds, both the cis (Z) and trans (E) isomers are within the scope of this invention. In cases wherein compounds may exist in tautomeric forms, such as keto-enol tautomers, each tautomeric form is contemplated as being included within this invention whether existing in equilibrium or predominantly in one form.

When the structure of the compounds used in this invention includes an asymmetric carbon atom such compound can occur as racemates, racemic mixtures, and isolated single enantiomers. All such isomeric forms of these compounds are expressly included in this invention. Each stereogenic carbon may be of the R or S configuration. It is to be understood accordingly that the isomers arising from such asymmetry (e.g., all enantiomers and diastereomers) are included within the scope of this invention, unless indicated otherwise. Such isomers can be obtained in substantially pure form by classical separation techniques and by stereochemically controlled synthesis, such as those described in "*Enantiomers, Racemates and Resolutions*" by J. Jacques, A. Collet and S. Wilen, Pub. John Wiley & Sons, N Y, 1981. For example, the resolution may be carried out by preparative chromatography on a chiral column.

The subject invention is also intended to include use of all isotopes of atoms occurring on the compounds disclosed herein. Isotopes include those atoms having the same atomic number but different mass numbers. By way of general example and without limitation, isotopes of hydrogen include tritium and deuterium. Isotopes of carbon include carbon-13 and carbon-14.

It will be noted that any notation of a carbon in structures throughout this application, when used without further notation, are intended to represent all isotopes of carbon, such as $^{12}C$, $^{13}C$, or $^{14}C$. Furthermore, any compounds containing $^{13}C$ or $^{14}C$ may specifically have the structure of any of the compounds disclosed herein.

It will also be noted that any notation of a hydrogen in structures throughout this application, when used without further notation, are intended to represent all isotopes of hydrogen, such as $^{1}H$, $^{2}H$, or $^{3}H$. Furthermore, any compounds containing $^{2}H$ or $^{3}H$ may specifically have the structure of any of the compounds disclosed herein.

Isotopically-labeled compounds can generally be prepared by conventional techniques known to those skilled in the art or by processes analogous to those described in the Examples disclosed herein using appropriate isotopically-labeled reagents in place of the non-labeled reagents employed.

The compounds of the instant invention may be in a salt form. As used herein, a "salt" is salt of the instant compounds which has been modified by making acid or base, salts of the compounds. In the case of compounds used for treatment of cancer, the salt is pharmaceutically acceptable. Examples of pharmaceutically acceptable salts include, but are not limited to, mineral or organic acid salts of basic residues such as amines; alkali or organic salts of acidic residues such as phenols. The salts can be made using an organic or inorganic acid. Such acid salts are chlorides, bromides, sulfates, nitrates/nitrites, esters, phosphates, sulfonates, formates, tartrates, maleates, malates, citrates, benzoates, salicylates, ascorbates, and the like. Phenolate salts are the alkaline earth metal salts, sodium, potassium or lithium. The term "pharmaceutically acceptable salt" in this respect, refers to the relatively non-toxic, inorganic and organic acid or base addition salts of compounds of the present invention. These salts can be prepared in situ during the final isolation and purification of the compounds of the invention, or by separately treating a purified compound of the invention in its free base or free acid form with a suitable organic or inorganic acid or base, and isolating the salt thus formed. Representative salts include the hydrobromide, hydrochloride, sulfate, bisulfate, phosphate, nitrate/nitrite, ester, acetate, valerate, oleate, palmitate, stearate, laurate, benzoate, lactate, phosphate, tosylate, citrate, maleate, fumarate, succinate, tartrate, napthylate, mesylate, glucoheptonate, lactobionate, and laurylsulphonate salts and the like. (See, e.g., Berge et al. (1977) "Pharmaceutical Salts", *J. Pharm. Sci.* 66:1-19).

As used herein, "alkyl" includes both branched and straight-chain saturated aliphatic hydrocarbon groups having the specified number of carbon atoms and may be unsubstituted or substituted. The Alkyls are C1-C10 alkyls, or a subset or individual thereof. In a non-limiting example, where the alkyl is C1-05 as in "C1-C5 alkyl", it is defined to include groups having 1, 2, 3, 4 or 5 carbons in a linear or branched arrangement and specifically includes methyl, ethyl, n-propyl, isopropyl, n-butyl, t-butyl, and pentyl. Alkyl may optionally be substituted with phenyl or substituted phenyl to provide substituted or unsubstituted benzyl.

Heterocyclyl means a saturated or partially unsaturated monocyclic radical containing 3 to 8 ring atoms and preferably 5 to 6 ring atoms selected from carbon or nitrogen but not limited to pyrrolidine.

As used herein the term "aryl" refers to aromatic monocyclic or multicyclic groups containing from 5 to 15 carbon atoms. Aryl groups include, but are not limited to groups such as unsubstituted or substituted phenyl. When referring to said aryl being substituted, said substitution may be at any position on the ring, other than the point of attachment to the other ring system of a compound of the invention. Therefore, any hydrogen atom on the aryl ring may be substituted with a substituent defined by the invention. In embodiments where the aryl is a phenyl ring, said substitution may be at the meta- and/or ortho- and/or para-position relative to the point of attachment. Aryl may optionally be substituted with a heterocyclyl-C(O)— moiety which includes a pyrrolidinyl-C(O)— moiety.

The term "heteroaryl" as used herein, represents a stable monocyclic, bicyclic or polycyclic ring of up to 10 atoms in each ring, wherein at least one ring is aromatic and contains from 1 to 4 heteroatoms or particularly 1 to 2 heteroatoms selected from the group consisting of O, N and S. Bicyclic aromatic heteroaryl groups include phenyl, pyridine, pyrimidine or pyridazine rings that are (a) fused to a 6-membered aromatic (unsaturated) heterocyclic ring having one nitrogen atom; (b) fused to a 5- or 6-membered aromatic (unsaturated) heterocyclic ring having two nitrogen atoms; (c) fused to a 5-membered aromatic (unsaturated) heterocyclic ring having one nitrogen atom together with either one oxygen or one sulfur atom; or (d) fused to a 5-membered aromatic (unsaturated) heterocyclic ring having one heteroatom. selected from O, N or S. Heteroaryl groups within the scope of this definition include but are not limited to: benzoimidazolyl, benzofuranyl, benzofurazanyl, benzopyrazolyl, benzotriazolyl, benzothiophenyl, benzoxazolyl, carbazolyl, carbolinyl, cinnolinyl, furanyl, indolinyl, indolyl, indolazinyl, indazolyl, isobenzofuranyl, isoindolyl, isoquinolyl, isothiazolyl, isoxazolyl, naphthpyridinyl, oxadiazolyl, oxazolyl, oxazoline, isoxazoline, oxetanyl, pyranyl, pyrazinyl, pyrazolyl, pyridazinyl, pyridopyridinyl, pyridazinyl, pyridyl, pyrimidyl, pyrrolyl, quinazolinyl, quinolyl, quinoxalinyl, tetrazolyl, tetrazolopyridyl, thiadiazolyl, thiazolyl, thienyl, triazolyl, azetidinyl, aziridinyl, 1,4-dioxanyl, hexahydroazepinyl, dihydrobenzoimidazolyl, dihydrobenzofuranyl, dihydrobenzothiophenyl, dihydrobenzoxazolyl, dihydrofuranyl, dihydroimidazolyl, dihydroindolyl, dihydroisooxazolyl, dihydroisothiazolyl, dihydrooxadiazolyl, dihydrooxazolyl, dihydropyrazinyl, dihydropyrazolyl, dihydropyridinyl, dihydropyriinidinyl, dihydropyrrolyl, dihydroquinolinyl, dihydrotetrazolyl, dihydrothiadiazolyl, dihydrothiazolyl, dihydrothienyl, dihydrotriazolyl, dihydroazetidinyl, methylenedioxybenzoyl, tetrahydrofuranyl, tetrahydrothienyl, acridinyl, carbazolyl, cinnolinyl, quinoxalinyl, pyrrazolyl, indolyl, benzotriazolyl, benzothiazolyl, benzoxazolyl, isoxazolyl, isothiazolyl, furanyl, thienyl, benzothienyl, benzofuranyl, quinolinyl, isoquinolinyl, oxazolyl, isoxazolyl, indolyl, pyrazinyl, pyridazinyl, pyridinyl, pyrimidinyl, pyrrolyl, tetra-hydroquinoline. In cases where the heteroaryl substituent is bicyclic and one ring is non-aromatic or contains no heteroatoms, it is understood that attachment is via the aromatic ring or via the heteroatom containing ring, respectively. If the heteroaryl contains nitrogen atoms, it is understood that the corresponding N-oxides thereof are also encompassed by this definition.

In the compounds of the present invention, the alkyl, aryl, or heteroaryl groups can be further substituted by replacing one or more hydrogen atoms be alternative non-hydrogen groups. These include, but are not limited to, 1-4 groups selected from alkyl, alkoxy, halo, hydroxy, mercapto, amino, carboxy, cyano and carbamoyl.

The term "substituted" refers to a functional group as described above in which one or more bonds to a hydrogen atom contained therein are replaced by a bond to non-hydrogen or non-carbon atoms, provided that normal valencies are maintained and that the substitution results in a stable compound. Substituted groups also include groups in which one or more bonds to a carbon (s) or hydrogen (s) atom are replaced by one or more bonds, including double or triple bonds, to a heteroatom. Examples of substituent groups include the functional groups described above, and, in particular, halogens (i.e., F, Cl, Br, and I); alkyl groups, such as methyl, ethyl, n-propyl, isopropryl, n-butyl, tert-butyl, and trifluoromethyl; hydroxyl; alkoxy groups, such as methoxy, ethoxy, n-propoxy, and isopropoxy; aryloxy groups, such as phenoxy; arylalkyloxy, such as benzyloxy (phenylmethoxy) and p-trifluoromethylbenzyloxy (4-trifluoromethylphenylmethoxy); heteroaryloxy groups; sulfonyl groups, such as trifluoromethanesulfonyl, methanesulfonyl, and p-toluenesulfonyl; nitro, nitrosyl; mercapto; sulfanyl groups, such as methylsulfanyl, ethylsulfanyl and propylsulfanyl; cyano; heterocyclyl-C(O)-moiety; amino groups, such as amino, methylamino, dimethylamino, ethylamino, and diethylamino; and carboxyl. Where multiple substituent moieties are disclosed or claimed, the substituted compound can be independently substituted by one or more of the disclosed or claimed substituent moieties, singly or plurally. By independently substituted, it is meant that the (two or more) substituents can be the same or different.

It is understood that substituents and substitution patterns on the compounds of the instant invention can be selected by one of ordinary skill in the art to provide compounds that are chemically stable and that can be readily synthesized by techniques known in the art, as well as those methods set forth below, from readily available starting materials. If a substituent is itself substituted with more than one group, it is understood that these multiple groups may be on the same carbon or on different carbons, so long as a stable structure results.

In choosing the compounds of the present invention, one of ordinary skill in the art will recognize that the various substituents, i.e. $R_1$, $R_2$, etc. are to be chosen in conformity with well-known principles of chemical structure connectivity. Moreover, where hydrogens are not shown in the carbon-based structures herein, implicit hydrogens are understood to complete valences as required.

The compounds of the instant invention may be in a salt form. As used herein, a "salt" is salt of the instant compounds which has been modified by making acid or base, salts of the compounds. In the case of compounds used for treatment of cancer, the salt is pharmaceutically acceptable. Examples of pharmaceutically acceptable salts include, but are not limited to, mineral or organic acid salts of basic residues such as amines; alkali or organic salts of acidic residues such as phenols. The salts can be made using an organic or inorganic acid. Such acid salts are chlorides, bromides, sulfates, nitrates/nitrites, esters, phosphates, sulfonates, formates, tartrates, maleates, malates, citrates, benzoates, salicylates, ascorbates, and the like. Phenolate salts are the alkaline earth metal salts, sodium, potassium or lithium. The term "pharmaceutically acceptable salt" in this respect, refers to the relatively non-toxic, inorganic and organic acid or base addition salts of compounds of the present invention. These salts can be prepared in situ during the final isolation and purification of the compounds of the invention, or by separately reacting a purified compound of the invention in its free base or free acid form with a suitable organic or inorganic acid or base, and isolating the salt thus formed. Representative salts include the hydrobromide, hydrochloride, sulfate, bisulfate, phosphate, nitrate/nitrite, ester, acetate, valerate, oleate, palmitate, stearate, laurate, benzoate, lactate, phosphate, tosylate, citrate, maleate, fumarate, succinate, tartrate, napthylate, mesylate, glucoheptonate, lactobionate, and laurylsulphonate salts and the like. (See, e.g., Berge et al. (1977) "Pharmaceutical Salts", J". Pharm. Sci. 66:1-19).

Where a numerical range is provided herein for any parameter, it is understood that all numerical subsets of that numerical range, and all the individual integer values contained therein, are provided as part of the invention. Thus, C1-C10 alkyl includes the subset of alkyls which are 1-3 carbon atoms, the subset of alkyls which are 2-5 carbon atoms etc. as well as an alkyl which has 1 carbon atom, an alkyl which has 3 carbon atoms, an alkyl which has 10 carbon atom, etc.

In an embodiment, the purines discussed herein are one or more of adenosine, inosine, hypoxanthine, or adenine. In an embodiment, "determining" as used herein means experimentally determining.

The term "composition", as in pharmaceutical composition, is intended to encompass a product comprising the active ingredient(s), and the inert ingredient(s) (pharmaceutically acceptable excipients) that make up the carrier, as well as any product which results, directly or indirectly, from combination, complexation or aggregation of any two or more of the ingredients, or from dissociation of one or more of the ingredients, or from other types of reactions or interactions of one or more of the ingredients. Accordingly, the pharmaceutical compositions of the present invention encompass any composition made by admixing a compound of Formula I, Formula II, Formula III, Formula IV, Formula V, Formula IV, Formula VII, or Formula VIII, and pharmaceutically acceptable excipients.

As used herein, the term "optionally" means that the subsequently described event(s) may or may not occur, and includes both event(s), which occur, and events that do not occur.

As used herein, the term "substituted with one or more groups" refers to substitution with the named substituent or substituents, multiple degrees of substitution, up to replacing all hydrogen atoms with the same or different substituents, being allowed unless the number of substituents is explicitly stated. Where the number of substituents is not explicitly stated, one or more is intended.

As used herein, "a compound of the invention" means a compound of Formula I, Formula II, Formula III, Formula IV, Formula V, Formula IV, Formula VII, or Formula VIII, or a salt, solvate or physiologically functional derivative thereof.

As used herein, the term "solvate" refers to a complex of variable stoichiometry formed by a solute (in this invention, a compound of Formula I, Formula II, Formula III, Formula IV, Formula V, Formula IV, Formula VII, or Formula VIII, or a salt thereof) and a solvent. Such solvents for the purpose of the invention may not interfere with the biological activity of the solute. Examples of suitable solvents include, but are not limited to, water, acetone, methanol, ethanol and acetic acid. Preferably the solvent used is a pharmaceutically acceptable solvent. Examples of suitable pharmaceutically acceptable solvents include water, ethanol and acetic acid. Most preferably the solvent is water.

As used herein, the term "physiologically functional derivative" refers to a compound (e.g, a drug precursor) that is transformed in vivo to yield a compound of Formula I, Formula II, Formula III, Formula IV, Formula V, Formula IV, Formula VII, or Formula VIII, or a pharmaceutically acceptable salt, hydrate or solvate of the compound. The transformation may occur by various mechanisms (e.g., by metabolic or chemical processes), such as, for example, through hydrolysis in blood. Prodrugs are such derivatives, and a discussion of the use of prodrugs is provided by T. Higuchi and W. Stella, "Pro-drugs as Novel Delivery Systems," Vol. 14 of the A.C.S. Symposium Series, and in Bioreversible Carriers in Drug Design, ed. Edward B. Roche, American Pharmaceutical Association and Pergamon Press, 1987.

All combinations of the various elements described herein are within the scope of the invention unless otherwise indicated herein or otherwise clearly contradicted by context. Whilst the embodiments for each variable have generally been listed above separately for each variable, this invention also includes those compounds in which several or each embodiment for compounds of Formula I, Formula II, Formula III, Formula IV, Formula V, Formula IV, Formula VII, or Formula VIII, is selected from each of the embodiments listed above. Therefore, this invention is intended to include all combinations of embodiments for each variable.

Any number of means for inhibiting G6PD activity or gene expression can be used in the methods of the invention. It is noted that in addition to G6PD, G6PD isoforms or 6-phosphogluconorate dehydrogenase and other enzymes in glucose (for example: malic enzyme or isocitrate dehydrogenase) and fat metabolism (for example: malony-CoA and HMG-CoA) including cholesterol synthesis is another process which could potentially be blocked by inhibitory compounds in a similar manner as described herein for G6PD.

Cardiovascular Diseases

The methods of the present invention may be used to treat a subject having or at risk for cardiovascular disorders or cardiovascular diseases.

Cardiovascular disorders or cardiovascular diseases can include any disorders that affect the cardiovascular system, including the heart and/or blood vessels, such as arteries and veins. Cardiovascular diseases can also include disorders affecting the kidneys. Non-limiting examples of cardiovascular diseases include pulmonary hypertension, pulmonary hypertension-associated heart failure, hypertension, stroke, medial hypertrophy, acute neointimal formation following iatrogenic interventions, atherosclerosis, congestive heart failure, heart failure, arrhythmia including atrial fibrillation, myocardial infarction, myocardial ischemia, cardiac hypertrophy, coronary heart disease, cardiac fibrosis, cardiomyopathy, ischemic heart disease, hypertensive heart disease, inflammatory heart disease, valvular heart disease, diseases of the cardiac valves, atherosclerosis, cardiorenal disease, vascular damage, myocardial damage, cardiac valvular disease or other cardiac electrophysiologic abnormalities, hypertension, other cardiac dysfunction, and combinations thereof. Cardiovascular disease can include, but is not limited to, right-sided, left-sided failure or congestive heart failure and could be due to any one of a number of different causes. Any type of cardiovascular disease, which includes impaired functioning of either the left or right ventricle is also encompassed herein. In some embodiments, cardiovascular diseases include diabetes mellitus, hyperhomocysteinemia and hypercholesterolemia.

Non-limiting examples of cardiovascular diseases that may be treated by the present composition and method also include angiosarcoma, hemangioscarcoma, Timothy Syndrome, hypertrophic cardiomyopathy, and combinations thereof.

Pulmonary hypertension includes pulmonary hypertension groups 1-5, including scleroderma, which is a member of group 1 pulmonary hypertension and is an autoimmune condition. (See: Ryan, John J. et al. "The WHO Classification of Pulmonary Hypertension: A Case-Based Imaging Compendium." *Pulmonary Circulation* 2.1 (2012): 107-121. PMC. Web. 16 Nov. 2016.)

Cardiomyopathies can include, but are not limited to, alcoholic cardiomyopathy, coronary artery disease, congenital heart disease, ischemic cardiomyopathy (ICM), dilated cardiomyopathy (DCM), hypertensive cardiomyopathy, valvular cardiomyopathy, inflammatory cardiomyopathy, diabetic cardiomyopathy and myocardiodystrophy, as well as other forms of cardiomyopathies.

Hypertensive heart diseases can include, but are not limited to, left ventricular hypertrophy, coronary heart disease, heart failure (including congestive), hypertensive cardiomyopathy, cardiac arrhythmias and renal disorders.

Inflammatory heart diseases can include, but are not limited to, endocarditis, inflammatory cardiomegaly and myocarditis.

Combination Therapy

The present composition may be administered alone or in combination with a second agent/treatment method (therapeutic intervention).

Therapeutic interventions that may be used in combination with the present composition or method can include, pharmacologic intervention, devices, surgical intervention, or any combination thereof. Pharmacologic interventions may include, but are not limited to, treatment with diuretics, vasodilators, inotropic agents (i.e., compounds that increase cardiac contractility), ACE inhibitors, beta-blockers, neurohumoral blockers (e.g., beta-blockers, angiotensin converting enzyme inhibitors), aldosterone antagonists (e.g., spironolactone, eplerenone), histone deactylase inhibitors, and erythropoietin. Devices may include, e.g., a bi-ventricular pacemarker, implantable cardioverter-defibrillator (ICD), ventricular assist device (VAD), left ventricular assist device (LVAD), or cardiac resynchronization therapy (CRT). Surgical interventions may include, heart transplantation, artificial heart, etc.

In certain embodiments, therapeutic intervention can be implantation of a medical device or surgical, which includes, for example, preventative, diagnostic or staging, curative and palliative surgery. Surgery may be used in conjunction with other therapies, including one or more other agents as described herein. Such surgical therapeutic agents for vascular and cardiovascular diseases and disorders are well known to those of skill in the art, and may include, but are not limited to, providing a cardiovascular mechanical prosthesis, angioplasty, coronary artery reperfusion, catheter ablation, providing an implantable cardioverter defibrillator to the subject, mechanical circulatory support or a combination thereof. Examples of a mechanical circulatory support that may be used in the present invention comprise an intra-aortic balloon counterpulsation, left ventricular assist device (LVAD) or combinations thereof.

Pharmacologic agents for therapeutic interventions can include, but are not limited to, miRNA based therapeutics (including antisense oligonucleotides), antihyperlipoproteinemic agent, an antiarteriosclerotic agent, an antithrombotic/fibrinolytic agent, a blood coagulant, an antiarrhythmic agent, an antihypertensive agent, a vasopressor, a treatment agent for congestive heart failure, an antianginal agent, an antibacterial agent or a combination thereof. U.S. Patent Application No. 2010/0317713.

An antihyperlipoproteinemic may be an agent that lowers the concentration of one of more blood lipids and/or lipoproteins. Examples of antihyperlipoproteinemics can include but are not limited to, acifran, azacosterol, benfluorex, p-benzalbutyramide, carnitine, chondroitin sulfate, clomestrone, detaxtran, dextran sulfate sodium, 5, 8, 11, 14, 17-eicosapentaenoic acid, eritadenine, furazabol, meglutol, melinamide, mytatrienediol, ornithine, y-oryzanol, pantethine, pentaerythritol tetraacetate, alpha-phenylbutyramide, pirozadil, probucol (lorelco), p-sitosterol, sultosilic acid-piperazine salt, tiadenol, triparanol and xenbucin. In some embodiments, antihyperlipoproteinemic agents can further comprise an aryloxyalkanoicifibric acid derivative, a resin/bile acid sequesterant, an HMG CoA reductase inhibitor, a nicotinic acid derivative, a thyroid hormone or thyroid hormone analog, a miscellaneous agent or a combination thereof.

In another embodiment, administration of an agent that aids in the removal or prevention of blood clots may be combined with administration of a modulator, particularly in treatment of athersclerosis and vasculature (e.g., arterial) blockages. Examples of antithrombotic and/or fibrinolytic agents can include but are not limited to anticoagulants, anticoagulant antagonists, antiplatelet agents, thrombolytic agents, throinbolytic agent antagonists or combinations thereof. Antithrombotic agents that can be included are those that are administered orally, such as, for example, aspirin and warfarin (coumadin).

Anticoagulants can include but are not limited to acenocoumarol, ancrod, anisindione, bromindione, clorindione, coumetarol, cyclocumarol, dextran sulfate sodium, dicumarol, diphenadione, ethyl biscoumacetate, ethylidene dicoumarol, fluindione, heparin, hirudin, lyapolate sodiuim, oxazidione, pentosan polysulfate, phenindione, phenprocoumon, phosvitin, picotamide, tioclomarol and warfarin.

Antiplatelet agents can include but are not limited to aspirin, a dextran, dipyridamole (persantin), heparin, sulfinpyranone (anturane) and ticlopidine (ticlid).

Thrombolytic agents can include but are not limited to tissue plasminogen activator (activase), plasmin, pro-urokinase, urokinase (abbokinase) streptokinase (streptase) and anistreplasel APSAC (eminase).

In one embodiment, the therapeutic intervention is an antiarrhythmic agent. Antiarrhythmic agents can include, but are not limited to Class I antiarrhythmic agents (sodium channel blockers), Class II antiarrhythmic agents (beta-adrenergic blockers), Class III antiarrhythmic agents (repolarization prolonging drugs), Class IV antiarrhythmic agents (calcium channel blockers) and miscellaneous antiarrhythric agents. Examples of sodium channel blockers can include but are not limited to Class IA, Class IB and Class IC antiarrhythmic agents. Non-limiting examples of Class IA antiarrhythmic agents include disppyramide (norpace), procainamide (pronestyl) and quinidine (quinidex). Examples of Class IB antiarrhythmic agents can include but are not limited to lidocaine (xylocalne), tocamide (tonocard) and mexiletine (mexitil). Examples of Class IC antiarrhythmic agents can include but are not limited to encamide (enkaid) and flecamide (tambocor).

Examples of a beta blocker, otherwise known as a p-adrenergic blocker, a p-adrenergic antagonist or a Class II antiarrhythmic agent, can include but are not limited to acebutolol (sectral), alprenolol, amosulalol, arotinolol, atenolol, befunolol, betaxolol, bevantolol, bisoprolol, bopindolol, bucumolol, bufetolol, bufuralol, bunitrolol, bupranolol, butidrine hydrochloride, butofilolol, carazolol, carteolol, carvedilol, celiprolol, cetamolol, cloranolol, dilevalol, epanolol, esmolol (brevibloc), indenolol, labetalol, levobunolol, mepindolol, metipranolol, metoprolol, moprolol, nadolol, nadoxolol, nifenalol, nipradilol, oxprenolol, penbutolol, pindolol, practolol, pronethalol, propanolol (inderal), sotalol (betapace), sulfinalol, talinolol, tertatolol, timolol, toliprolol and xibinolol. In some embodiments, the beta blocker can comprise an aryloxypropanolamine derivative. Examples of aryloxypropanolamine derivatives can include but are not limited to acebutolol, alprenolol, arotinolol, atenolol, betaxolol, bevantolol, bisoprolol, bopindolol, bunitrolol, butofilolol, carazolol, carteolol, carvedilol, celiprolol, cetamolol, epanolol, indenolol, mepindolol, metipranolol, metoprolol, mrnoprolol, nadolol, nipradilol, oxprenolol, penbutolol, pindolol, propanolol, talinolol, tertatolol, tinolol and toliprolol.

Examples of agents that prolong repolarization, also known as a Class III antiarrhythmic agent, can include but are not limited to include amiodarone (cordarone) and sotalol (betapace).

Examples of a calcium channel blocker, otherwise known as a Class IV antiarrhythmic agent, can include but are not limited to an arylalkylamine (e.g., bepridile, diltiazem, fendiline, gallopamil, prenylamine, terodiline, verapamil), a dihydropyridine derivative (felodipine, isradipine, nicardipine, nifedipine, nimodipine, nisoldipine, nitrendipine) a piperazinde derivative (e.g., cinnarizine, flunarizine, lidoflazine) or a micellaneous calcium channel blocker such as bencyclane, etafenone, magnesium, mibefradil or perhexyline. In some embodiments, a calcium channel blocker comprises a long-acting dihydropyridine (nifedipine-type) calcium antagonist.

Examples of antihypertensive agents can include but are not limited to sympatholytic, alpha/beta blockers, alpha-blockers, anti-angiotensin II agents, beta blockers, calcium channel blockers, vasodilators and miscellaneous antihypertensives.

Examples of an alpha blocker, also known as an α-adrenergic blocker or an α-adrenergic antagonist, can include but are not limited to, amosulalol, arotinolol, dapiprazole, doxazosin, ergoloid mesylates, fenspiride, indoramin, labetalol, nicergoline, prazosin, terazosin, tolazoline, trimazosin and yohimbine. In certain embodiments, an alpha-blocker may comprise a quinazoline derivative. Quinazoline derivatives can include but are not limited to alfuzosin, bunazosin, doxazosin, prazosin, terazosin and trimazosin. The antihypertensive agent may be both an alpha and beta-adrenergic antagonist. Examples of an alpha/beta blocker can include but are not limited to labetalol (normodyne, trandate).

Examples of anti-angiotensin II agents can include but are not limited to angiotensin converting enzyme inhibitors and angiotensin II receptor antagonists. Angiotensin converting enzyme inhibitors (ACE inhibitors) can include but are not limited to alacepril, enalapril (vasotec), captopril, cilazapril, delapril, enalaprilat, fosinopril, lisinopril, moveltopril, perindopril, quinapril and ramipril. Examples of an angiotensin II receptor blocker, also known as an angiotensin II receptor antagonist, an ANG receptor blocker or an ANG-II type-I receptor blocker (ARBS), include but are not limited to angiocandesartan, eprosartan, irbesartan, losartan and valsartan.

Examples of a sympatholytic include a centrally acting sympatholytic or a peripherially acting sympatholytic. Examples of a centrally acting sympatholytic, also known as a central nervous system (CNS) sympatholytic, can include but are not limited to clonidine (catapres), guanabenz (wytensin) guanfacine (tenex) and methyldopa (aldomet).

Examples of a peripherally acting sympatholytic can include but are not limited to a ganglion blocking agent, an adrenergic neuron blocking agent, beta-adrenergic blocking agent or an alphal-adrenergic blocking agent. Examples of a ganglion blocking agent include mecarnylamine (inversine) and trimethaphan (arfonad). Examples of an adrenergic neuron blocking agent can include but are not limited to guanethidine (ismelin) and reserpine (serpasil).

Examples of a beta-adrenergic blocker can include but are not limited to acenitolol (sectral), atenolol (tenormin), betaxolol (kerlone), carteolol (cartrol), labetalol (normodyne, trandate), metoprolol (lopressor), nadanol (corgard), penbutolol (levatol), pindolol (visken), propranolol (inderal) and timolol (blocadren).

Examples of alphal-adrenergic blocker can include but are not limited to prazosin (minipress), doxazocin (cardura) and terazosin (hytrin).

The therapeutic intervention can also comprise a vasodilator (e.g., a cerebral vasodilator, a coronary vasodilator or a peripheral vasodilator). In other embodiments, a vasodilator comprises a coronary vasodilator. Examples of a coronary vasodilator include but are not limited to amotriphene, bendazol, benfurodil hemisuccinate, benziodarone, chloracizine, chromonar, clobenfurol, clonitrate, dilazep, dipyridamole, droprenilamine, efloxate, erythrityl tetranitrane, etafenone, fendiline, floredil, ganglefene, herestrol bis(p-dinoeylaminoethyl ether), hexobendine, itramin tosylate, khellin, lidoflanine, mannitol hexanitrane, medibazine, nicorglycerin, pentaerythritol tetranitrate, pentrinitrol, perhexyline, pimefyiline, trapidil, tricromyl, trimeG6PDidine, trolnitrate phosphate and visnadine. In some embodiments, a vasodilator can comprise a chronic therapy vasodilator or a hypertensive emergency vasodilator. Examples of a chronic therapy vasodilator can include but are not limited to hydralazine (apresoline) and minoxidil (loniten). Examples of a hypertensive emergency vasodilator can include but are not limited to nitroprusside (nipride), diazoxide (hyperstat IV), hydralazine (apresoline), minoxidil (loniten) and verapamil Examples of antihypertensives can also include, but are not limited to, ajmaline, gamma-amino butyric acid, bufeniode, cicletainine, ciclosidomine, a cryptenamine tannate, fenoldopam, flosequinan, ketanserin, mebutamate, mecamylamine, methyldopa, methyl 4-pyridyl ketone thiosemicarbazone, muzo limine, pargyline, pempidine, pinacidil, piperoxan, primaperone, a protoveratrine, raubasine, rescimetol, rilmenidene, saralasin, sodium nitrorusside, ticrynafen, trimethaphan camsylate, tyrosinase and urapidil.

In certain embodiments, an antihypertensive can comprise an arylethanolamine derivative, a benzothiadiazine derivative, a N-carboxyalkyl(peptide/lactam) derivative, a dihydropyridine derivative, a guanidine derivative, a hydrazines/phthalazine, an imidazole derivative, a quaternary ammoniam compound, a reserpine derivative or a suflonamide derivative. Examples of arylethanolamine derivatives can include but are not limited to amosulalol, bufuralol, dilevalol, labetalol, pronethalol, sotalol and sulfinalol. Examples of benzothiadiazine derivatives can include but are not limited to althizide, bendroflumethazide, benzthiazide, benzylhydrochlorothiazide, buthiazide, chlorothiazide, chlorthalidone, cyclopenthiazide, cyclothiazide, diazoxide, epithiazide, ethiazide, fenquizone, hydrochlorothiazide, hydroflumethizide, methyclothiazide, meticrane, metolazone, paraflutizide, polythizide, tetrachlormethiazide and trichlormethiazide. Examples of N-carboxyalkyl(peptide/lactam) derivatives can include but are not limited to alacepril, captopril, cilazapril, delapril, enalapril, enalaprilat, fosinopril, lisinopril, moveltipril, perindopril, quinapril and ramipril. Examples of dihydropyridine derivatives can include but are not limited to amlodipine, felodipine, isradipine, nicardipine, nifedipine, nilvadipine, nisoldipine and nitrendipine. Examples of guanidine derivatives can include but are not limited to bethanidine, debrisoquin, guanabenz, guanacline, guanadrel, guanazodine, guanethidine, guanfacine, guanochlor, guanoxabenz and guanoxan. Examples of hydrazines/phthalazines can include but are not limited to budralazine, cadralazine, dihydralazine, endralazine, hydracarbazine, hydralazine, pheniprazine, pildralazine and todralazine. Examples of imidazole derivatives can include but are not limited to clonidine, lofexidine, phentolamine, tiamenidine and tolonidine. Examples of quaternary ammonium compounds can include but are not limited to azamethonium bromide, chlorisondamine chloride, hexamethonium, pentacynium bis(methylsulfate), pentamethoniumi bromide, pentolinium tartrate, phenactropiniutm chloride and trimethidinium methosulfate. Examples of reserpine derivatives can include but are not limited to bietaserpine, deserpidine, rescinnamine, reserpine and syrosingopine. Examples of sulfonamide derivatives can include but are not limited to ambuside, clopamide, furosemide, indapamide, quinethazone, trip amide and xipamide.

Examples of agents for the treatment of congestive heart failure can include but are not limited to anti-angiotensin II agents, afterload-preload reduction treatment, diuretics and inotropic agents.

Examples of a diuretic can include but are not limited to a thiazide or benzothiadiazine derivative (e.g., althiazide, bendroflumethazide, benzthiazide, benzylhydrochiorchlorothiazide, buthiazide, chlorothiazide, chlorothiazide, chlorthalidone, cyclopenthiazide, epithiazide, ethiazide, ethiazide, fenquizone, hydrochlorothiazide, hydroflumethiazide, methyclothiazide, meticrane, metolazone, paraflutizide, polythizide, tetrachloromethiazide, trichlormethiazide), an organomercurial (e.g., chlormerodrin, meralluride, mercamnphamide, mercaptomerin sodium, mercumallylic acid, mercumatilin dodium, mercurous chloride, mersalyl), a pteridine (e.g., furtherene, triamterene), purines (e.g., acefylline, 7-morpholinomethyltheophylline, pamobrom, protheobromine, theobromine), steroids including aldosterone antagonists (e.g., canrenone, oleandrin, spironolactone), a sulfonamide derivative (e.g., aceG6PDolamide, ambuside, azosemide, bumetanide, buG6PDolamide, chloraminophenami de, clofenamide, clopamide, clorexolone, diphenylmethane-4,4'-disulfonamide, disulfamide, ethoxzolamide, furosemide, indapamide, mefruside, methazolamide, piretanide, quinethazone, torasemide, trip amide, xipamide), a uracil (e g, aminometradine, amisometradine), a potassium sparing antagonist (e.g., amiloride, triamterene) or a miscellaneous diuretic such as aminozine, arbutin, chlorazanil, ethacrynic acid, etozolin, hydracarbazine, isosorbide, mannitol, metochalcone, muzo limine, perhexyline, ticmafen and urea.

Examples of a positive inotropic agent, also known as a cardiotonic, can include but are not limited to acefylline, an acetyldigitoxin, 2-amino-4-picoline, aminone, benfurodil hemisuccinate, bucladesine, cerberosine, camphotamide, convallatoxin, cymarin, denopamine, deslanoside, digitalin, digitalis, digitoxin, digoxin, dobutamine, dopamine, dopexamine, enoximone, erythrophleine, fenalcomine, gitalin, gitoxin, glycocyamine, heptaminol, hydrastinine, ibopamine, a lanatoside, metamivam, milrinone, nerifolin, oleandrin, ouabain, oxyfedrine, prenalterol, proscillaridine, resibufogenin, scillaren, scillarenin, strphanthin, sulmazole, theobromine and xamoterol. In some embodiments, an intropic agent is a cardiac glycoside, a beta-adrenergic agonist or a phosphodiesterase inhibitor. Examples of a cardiac glycoside can include but are not limited to digoxin (lanoxin) and digitoxin (crystodigin). Examples of a .beta.-adrenergic agonist include but are not limited to albuterol, bambuterol, bitolterol, carbuterol, clenbuterol, clorprenaline, denop amine, dioxethedrine, dobutamine (dobutrex), dopamine (intropin), dopexamine, ephedrine, etafedrine, ethylnorepinephrine, fenoterol, formoterol, hexoprenaline, ibopamine, isoetharine, isoproterenol, mabuterol, metaproterenol, methoxyphenamine, oxyfedrine, pirbuterol, procaterol, protokylol, reproterol, rimiterol, ritodrine, soterenol, terbutaline, tretoquinol, tulobuterol and xamoterol. Examples of a phosphodiesterase inhibitor can include but are not limited to aminone (inocor).

Antianginal agents may comprise organonitrates, calcium channel blockers, beta blockers and combinations thereof. Examples of organonitrates, also known as nitrovasodilators, can include but are not limited to nitroglycerin (nitrobid, nitrostat), isosorbide dinitrate (isordil, sorbitrate) and amyl nitrate (aspirol, vaporole).

Endothelin (ET) is a 21-amino acid peptide that has potent physiologic and pathophysiologic effects that appear to be involved in the development of heart failure. The effects of ET are mediated through interaction with two classes of cell surface receptors. Inhibiting the ability of ET to stimulate cells involves the use of agents that block the interaction of ET with its receptors. Examples of endothelin receptor antagonists (ERA) can include but are not limited to Bosentan, Enrasentan, Ambrisentan, Darusentan, Tezosentan, Atrasentan, Avosentan, Clazosentan, Edonentan, sitaxsentan, TBC 3711, BQ 123, and BQ 788.

Histone deacetylase inhibitors that appear to have beneficial effects the treatment of pulmonary hypertension. Examples of histone deacetylase inhibitors can include but are not limited to valproic acid and suberoylanilide hydroxamic acid.

Evidence of therapeutic efficacy may be specific to the cardiovascular disease being treated and can include evidence well known in the art. For example, evidence of therapeutic efficacy can include but is not limited to improvement or alleviation of one or more symptoms of cardiac hypertrophy, heart failure, or myocardial infarction in the subject, or in the delay in the transition from cardiac hypertrophy to heart failure. The one or more improved or alleviated symptoms can include, for example, increased exercise capacity, increased cardiac ejection volume, decreased left ventricular end diastolic pressure, decreased pulmonary capillary wedge pressure, increased cardiac output, increased cardiac index, lowered pulmonary artery pressures, decreased left ventricular end systolic and diastolic dimensions, decreased cardiac fibrosis, decreased collagen deposition in cardiac muscle, decreased left and right ventricular wall stress, decreased wall tension, increased quality of life, and decreased disease related morbidity or mortality. Further, therapeutic efficacy can also include general improvements in the overall health of the patient, such as but not limited to enhancement of patient life quality, increase in predicted survival rate, decrease in depression or decrease in rate of recurrence of the indication (Physicians' Desk Reference (2010).

Efficacy of a therapeutic intervention can also include evaluating or monitoring for the improvement of one or more symptoms of cardiac hypertrophy, heart failure, or myocardial infarction in the subject, or for the delay in the transition from cardiac hypertrophy to heart failure. The one or more improved symptoms may include, for example, increased exercise capacity, increased cardiac ejection volume, decreased left ventricular end diastolic pressure, decreased pulmonary capillary wedge pressure, increased cardiac output, increased cardiac index, lowered pulmonary artery pressures, decreased left ventricular end systolic and diastolic dimensions, decreased cardiac fibrosis, decreased collagen deposition in cardiac muscle, decreased left and right ventricular wall stress, decreased wall tension, increased quality of life and decreased disease related morbidity or mortality. The measured levels of plasma miRNAs may serve as a surrogate marker for efficacy of the therapeutic intervention.

Definitions

So that the invention may be more readily understood, certain technical and scientific terms are specifically defined below. Unless specifically defined elsewhere in this document, all other technical and scientific terms used herein have the meaning commonly understood by one of ordinary skill in the art to which this invention belongs.

As used herein, including the appended claims, the singular forms of words such as "a," "an," and "the," include their corresponding plural references unless the context clearly dictates otherwise.

"Activation," "stimulation," and "treatment," as it applies to cells or to receptors, may have the same meaning, e.g., activation, stimulation, or treatment of a cell or receptor with a ligand, unless indicated otherwise by the context or explicitly. "Ligand" encompasses natural and synthetic ligands, e.g., cytokines, cytokine variants, analogues, muteins, and binding compounds derived from antibodies. "Ligand" also encompasses small molecules, e.g., peptide mimetics of cytokines and peptide mimetics of antibodies. "Activation" can refer to cell activation as regulated by internal mechanisms as well as by external or environmental factors. "Response," e.g., of a cell, tissue, organ, or organism, encompasses a change in biochemical or physiological behavior, e.g., concentration, density, adhesion, or migration within a biological compartment, rate of gene expression, or state of differentiation, where the change is correlated with activation, stimulation, or treatment, or with internal mechanisms such as genetic programming.

"Activity" of a molecule may describe or refer to the binding of the molecule to a ligand or to a receptor, to catalytic activity; to the ability to stimulate gene expression or cell signaling, differentiation, or maturation; to antigenic activity, to the modulation of activities of other molecules, and the like. "Activity" of a molecule may also refer to activity in modulating or maintaining cell-to-cell interactions, e.g., adhesion, or activity in maintaining a structure of a cell, e.g., cell membranes or cytoskeleton. "Activity" can also mean specific activity, e.g., [catalytic activity]/[mg protein], or [immunological activity]/[mg protein], concentration in a biological compartment, or the like. "Activity" may refer to modulation of components of the innate or the adaptive immune systems.

"Administration" and "treatment," as it applies to an animal, human, experimental subject, cell, tissue, organ, or biological fluid, refers to contact of an exogenous pharmaceutical, therapeutic, diagnostic agent, or composition to the animal, human, subject, cell, tissue, organ, or biological fluid. "Administration" and "treatment" can refer, e.g., to therapeutic, pharmacokinetic, diagnostic, research, and experimental methods. Treatment of a cell encompasses contact of a reagent to the cell, as well as contact of a reagent to a fluid, where the fluid is in contact with the cell.

"Administration" and "treatment" also means in vitro and ex vivo treatments, e.g., of a cell, by a reagent, diagnostic, binding compound, or by another cell. The term "subject" includes any organism, preferably an animal, more preferably a mammal (e.g., rat, mouse, dog, cat, rabbit) and most preferably a human, including a human patient.

"Treat" or "treating" refers to administering a therapeutic agent, such as a composition containing any of the present G6PD inhibitors, or similar compositions described herein, internally or externally to a subject or patient having one or more disease symptoms, or being suspected of having a disease or being at elevated at risk of acquiring a disease, for which the agent has therapeutic activity. Typically, the agent is administered in an amount effective to alleviate one or more disease symptoms in the treated subject or population, whether by inducing the regression of or inhibiting the progression of such symptom(s) by any clinically measurable degree. The amount of a therapeutic agent that is effective to alleviate any particular disease symptom (also referred to as the "therapeutically effective amount") may vary according to factors such as the disease state, age, and weight of the patient, and the ability of the drug to elicit a desired response in the subject whether a disease symptom has been alleviated can be assessed by any clinical measurement typically used by physicians or other skilled healthcare providers to assess the severity or progression status of that symptom. While an embodiment of the present invention (e.g., a treatment method or article of manufacture) may not be effective in alleviating the target disease symptom(s) in every subject, it should alleviate the target disease symptom(s) in a statistically significant number of subjects as determined by any statistical test known in the art such as the Student's t-test, the chit-test, the U-test according to Mann and Whitney, the Kruskal-Wallis test (H-test), Jonckheere-Terpstra-test and the Wilcoxon-test.

"Treatment," as it applies to a human, veterinary, or research subject, refers to therapeutic treatment, prophylactic or preventative measures, to research and diagnostic applications.

As used herein, the expressions "cell," "cell line," and "cell culture" are used interchangeably and all such designations include progeny. Thus, the words "transformants" and "transformed cells" include the primary subject cell and cultures derived therefrom without regard for the number of transfers. It is also understood that not all progeny will have precisely identical DNA content, due to deliberate or inadvertent mutations. Mutant progeny that have the same function or biological activity as screened for in the originally transformed cell are included. Where distinct designations are intended, it will be clear from the context.

With respect to cells, the term "isolated" refers to a cell that has been isolated from its natural environment (e.g., from a tissue or subject). The term "cell line" refers to a population of cells capable of continuous or prolonged growth and division in vitro. Often, cell lines are clonal populations derived from a single progenitor cell. It is further known in the art that spontaneous or induced changes can occur in karyotype during storage or transfer of such clonal populations. Therefore, cells derived from the cell line referred to may not be precisely identical to the ancestral cells or cultures, and the cell line referred to includes such variants. As used herein, the terms "recombinant cell" refers to a cell into which an exogenous DNA segment, such as DNA segment that leads to the transcription of a biologically-active polypeptide or production of a biologically active nucleic acid such as an RNA, has been introduced.

Pharmaceutical Compositions and Administration

To prepare pharmaceutical or sterile compositions of the compositions of the present invention, the present compound may be admixed with a pharmaceutically acceptable carrier or excipient. See, e.g., *Remington's Pharmaceutical Sciences* and *U.S. Pharmacopeia: National Formulary*, Mack Publishing Company, Easton, Pa. (1984).

Formulations of therapeutic and diagnostic agents may be prepared by mixing with acceptable carriers, excipients, or stabilizers in the form of, e.g., lyophilized powders, slurries, amorphous solution or solid, aqueous solutions or suspensions (see, e.g., Hardman, et al. (2001) *Goodman and Gilman's The Pharmacological Basis of Therapeutics*, McGraw-Hill, New York, N.Y.; Gennaro (2000) *Remington: The Science and Practice of Pharmacy*, Lippincott, Williams, and Wilkins, New York, N.Y.; Avis, et al. (eds.) (1993) *Pharmaceutical Dosage Forms: Parenteral Medications*, Marcel Dekker, NY; Lieberman, et al. (eds.) (1990) *Pharmaceutical Dosage Forms: Tablets*, Marcel Dekker, NY; Lieberman, et al. (eds.) (1990) *Pharmaceutical Dosage Forms: Disperse Systems*, Marcel Dekker, NY; Weiner and Kotkoskie (2000) Excipient Toxicity and Safety, Marcel Dekker, Inc., New York, N.Y.).

Toxicity and therapeutic efficacy of the therapeutic compositions, administered alone or in combination with another agent, can be determined by standard pharmaceutical procedures in cell cultures or experimental animals, e.g., for determining the $LD_{50}$ (the dose lethal to 50% of the population) and the $ED_{50}$ (the dose therapeutically effective in 50% of the population). The dose ratio between toxic and therapeutic effects is the therapeutic index ($LD_{50}/ED_{50}$). In particular aspects, therapeutic compositions exhibiting high therapeutic indices are desirable. The data obtained from these cell culture assays and animal studies can be used in formulating a range of dosage for use in human. The dosage of such compounds lies preferably within a range of circulating concentrations that include the $ED_{50}$ with little or no toxicity. The dosage may vary within this range depending upon the dosage form employed and the route of administration.

In an embodiment of the invention, a composition of the invention is administered to a subject in accordance with the Physicians' Desk Reference 2003 (Thomson Healthcare; 57th edition (Nov. 1, 2002)).

The mode of administration can vary. Suitable routes of administration include intranasal, nasal, oral, rectal, transmucosal, intestinal, parenteral; intramuscular, subcutaneous, intradermal, intramedullary, intrathecal, direct intraventricular, intravenous, intraperitoneal, intraocular, inhalation, insufflation, topical, cutaneous, transdermal, or intra-arterial.

In particular embodiments, the composition or therapeutic can be administered by an invasive route such as by injection (see above). In further embodiments of the invention, the composition, therapeutic, or pharmaceutical composition thereof, is administered intravenously, subcutaneously, intramuscularly, intraarterially, intra-articularly (e.g. in arthritis joints), intratumorally, or by inhalation, aerosol delivery. Administration by non-invasive routes (e.g., orally; for example, in a pill, capsule or tablet) is also within the scope of the present invention.

Compositions can be administered with medical devices known in the art. For example, a pharmaceutical composition of the invention can be administered by injection with a hypodermic needle, including, e.g., a prefilled syringe or autoinjector.

The pharmaceutical compositions of the invention may also be administered with a needleless hypodermic injection device; such as the devices disclosed in U.S. Pat. No. 6,620,135; 6,096,002; 5,399,163; 5,383,851; 5,312,335; 5,064,413; 4,941,880; 4,790,824 or 4,596,556.

Alternately, one may administer the present compound or other G6PD inhibitors, or related compound in a local rather than systemic manner, for example, via injection of directly into the desired target site, often in a depot or sustained release formulation. Furthermore, one may administer the composition in a targeted drug delivery system, for example, in a liposome coated with a tissue-specific antibody, targeting, for example, the liver, and more specifically hepatocytes. The liposomes will be targeted to and taken up selectively by the desired tissue. Also included in a targeted drug delivery system is nanoparticle specific nasal or cardiac delivery of the viral vectors, RNAi, shRNA or other G6PD inhibitors, or G6PD-based compound, alone or in combination with an Ihh RNAi construct or similar inhibitors. A summary of various delivery methods and techniques of siRNA administration in ongoing clinical trials is provided in Zuckerman and Davis 2015; Nature Rev. Drug Discovery, Vol. 14: 843-856, December 2015.

The present composition can also comprise a delivery vehicle, including liposomes, for administration to a subject, carriers and diluents and their salts, and/or can be present in pharmaceutically acceptable formulations. For example, methods for the delivery of nucleic acid molecules are described in Akhtar et al., 1992, *Trends Cell Bio.*, 2, 139; DELIVERY STRATEGIES FOR ANTISENSE OLIGONUCLEOTIDE THERAPEUTICS, ed. Akbtar, 1995, Maurer et al., 1999, *Mol. Membr. Biol.*, 16, 129-140; Hofland and Huang, 1999, *Handb. Exp. Pharmacol.*, 137, 165-192; and Lee et al., 2000, ACS Symp. Ser., 752, 184-192. U.S. Pat. No. 6,395,713 and PCT Publication No. WO 94/02595 further describe the general methods for delivery of nucleic acid molecules. These protocols can be utilized for the delivery of virtually any nucleic acid molecule.

The present composition can be administered to a desired target by a variety of methods known to those of skill in the art, including, but not restricted to, encapsulation in liposomes, by iontophoresis, or by incorporation into other vehicles, such as hydrogels, cyclodextrins, biodegradable nanocapsules, and bioadhesive microspheres, or by proteinaceous vectors (see PCT Publication No. WO 00/53722). Alternatively, the therapeutic/vehicle combination is locally delivered by direct injection or by use of an infusion pump. Direct injection of the composition, whether subcutaneous, intramuscular, or intradermal, can take place using standard needle and syringe methodologies, or by needle-free technologies such as those described in Conry et al., 1999, Clin. Cancer Res., 5, 2330-2337 and PCT Publication No. WO 99/31262.

Therapeutic compositions comprising surface-modified liposomes containing poly(ethylene glycol) lipids (PEG-modified, or long-circulating liposomes or stealth liposomes) may also be suitably employed in the methods of the invention. These formulations offer a method for increasing the accumulation of drugs in target tissues. This class of drug carriers resists opsonization and elimination by the mononuclear phagocytic system (MPS or RES), thereby enabling longer blood circulation times and enhanced tissue exposure for the encapsulated drug (Lasic et al. Chem. Rev. 1995, 95, 2601-2627; Ishiwata et al., Chem. Pharm. Bull. 1995, 43, 1005-1011). The long-circulating liposomes enhance the pharmacokinetics and pharmacodynamics of DNA and RNA, particularly compared to conventional cationic liposomes which are known to accumulate in tissues of the MPS (Liu et al., J. Biol. Chem. 1995, 42, 24864-24870; PCT Publication No. WO 96/10391; PCT Publication No. WO 96/10390; and PCT Publication No. WO 96/10392). Long-circulating liposomes are also likely to protect drugs from nuclease degradation to a greater extent compared to cationic liposomes, based on their ability to avoid accumulation in metabolically aggressive MPS tissues such as the liver and spleen.

The administration regimen depends on several factors, including the serum or tissue turnover rate of the therapeutic composition, the level of symptoms, and the accessibility of the target cells in the biological matrix. Preferably, the administration regimen delivers sufficient therapeutic composition to effect improvement in the target disease state, while simultaneously minimizing undesired side effects. Accordingly, the amount of biologic delivered depends in part on the particular therapeutic composition and the severity of the condition being treated.

Determination of the appropriate dose is made by the clinician, e.g., using parameters or factors known or suspected in the art to affect treatment. Generally, the dose begins with an amount somewhat less than the optimum dose and it is increased by small increments thereafter until the desired or optimum effect is achieved relative to any negative side effects. Important diagnostic measures include those of symptoms of, e.g., the inflammation or level of inflammatory cytokines produced. In general, it is desirable that a biologic that will be used is derived from the same species as the animal targeted for treatment, thereby minimizing any immune response to the reagent.

As used herein, "inhibit" or "treat" or "treatment" includes a postponement of development of the symptoms associated with a disorder and/or a reduction in the severity of the symptoms of such disorder. The terms further include ameliorating existing uncontrolled or unwanted symptoms, preventing additional symptoms, and ameliorating or preventing the underlying causes of such symptoms. Thus, the terms denote that a beneficial result has been conferred on a vertebrate subject with a disorder, disease or symptom, or with the potential to develop such a disorder, disease or symptom.

As used herein, the terms "therapeutically effective amount", "therapeutically effective dose" and "effective amount" refer to an amount of the present compound or other G6PD inhibitors or inhibitor compound of the invention that, when administered alone or in combination with an additional therapeutic agent to a cell, tissue, or subject, is effective to cause a measurable improvement in one or more symptoms of a disease or condition or the progression of such disease or condition. A therapeutically effective dose further refers to that amount of the compound sufficient to result in at least partial amelioration of symptoms, e.g., treatment, healing, prevention or amelioration of the relevant medical condition, or an increase in rate of treatment, healing, prevention or amelioration of such conditions. When applied to an individual active ingredient administered alone, a therapeutically effective dose refers to that ingredient alone. When applied to a combination, a therapeutically effective dose refers to combined amounts of the active ingredients that result in the therapeutic effect, whether administered in combination, serially or simultaneously. An effective amount of a therapeutic will result in an improvement of a diagnostic measure or parameter by at least 10%; usually by at least 20%; preferably at least about 30%; more preferably at least 40%, and most preferably by at least 50%. An effective amount can also result in an improvement in a subjective measure in cases where subjective measures are used to assess disease severity.

Kits

The present invention also provides kits comprising the components of the combinations of the invention in kit form. A kit of the present invention includes one or more components including, but not limited to, one or more G6PD inhibitors as discussed herein, in association with one or more additional components including, but not limited to a pharmaceutically acceptable carrier and/or a chemotherapeutic agent, as discussed herein. The present compound, composition and/or the therapeutic agent can be formulated as a pure composition or in combination with a pharmaceutically acceptable carrier, in a pharmaceutical composition.

Kits may also include primers, buffers, and probes along with instructions for determining elevated levels of nucleic acid, proteins, or protein fragments of G6PD, or any combination thereof.

In one embodiment, a kit includes the present compounds/composition of the invention or a pharmaceutical composition thereof in one container (e.g., in a sterile glass or plastic vial) and a pharmaceutical composition thereof and/or a chemotherapeutic agent in another container (e.g., in a sterile glass or plastic vial).

In another embodiment of the invention, the kit comprises a combination of the invention, including the present compound or other G6PD inhibitors, or G6PD-based inhibitor compounds, along with a pharmaceutically acceptable carrier, optionally in combination with one or more therapeutic agent components formulated together, optionally, in a pharmaceutical composition, in a single, common container.

If the kit includes a pharmaceutical composition for parenteral administration to a subject, the kit can include a device for performing such administration. For example, the kit can include one or more hypodermic needles or other injection devices as discussed above.

The kit can include a package insert including information concerning the pharmaceutical compositions and dosage forms in the kit. Generally, such information aids patients and physicians in using the enclosed pharmaceutical compositions and dosage forms effectively and safely. For example, the following information regarding a combination of the invention may be supplied in the insert: pharmacokinetics, pharmacodynamics, clinical studies, efficacy parameters, indications and usage, contraindications, warnings, precautions, adverse reactions, overdosage, proper dosage and administration, how supplied, proper storage conditions, references, manufacturer/distributor information and patent information.

General Methods

Standard methods in molecular biology are described Sambrook, Fritsch and Maniatis (1982 & 1989 $2^{nd}$ Edition, 2001 $3^{rd}$ Edition) *Molecular Cloning, A Laboratory Manual*, Cold Spring Harbor Laboratory Press, Cold Spring Harbor, N.Y.; Sambrook and Russell (2001) *Molecular Cloning*, $3^{rd}$ ed., Cold Spring Harbor Laboratory Press, Cold Spring Harbor, N.Y.; Wu (1993) *Recombinant DNA*, Vol. 217, Academic Press, San Diego, Calif.). Standard methods also appear in Ausbel, et al. (2001) *Current Protocols in Molecular Biology, Vols.* 1-4, John Wiley and Sons, Inc. New York, N.Y., which describes cloning in bacterial cells and DNA mutagenesis (Vol. 1), cloning in mammalian cells and yeast (Vol. 2), glycoconjugates and protein expression (Vol. 3), and bioinformatics (Vol. 4).

Methods for protein purification including immunoprecipitation, electrophoresis, centrifugation, and crystallization are described (Coligan, et al. (2000) *Current Protocols in Protein Science, Vol.* 1, John Wiley and Sons, Inc., New York). Chemical analysis, chemical modification, post-translational modification, production of fusion proteins, glycosylation of proteins are described (see, e.g., Coligan, et al. (2000) *Current Protocols in Protein Science, Vol.* 2, John Wiley and Sons, Inc., New York; Ausubel, et al. (2001) *Current Protocols in Molecular Biology, Vol.* 3, John Wiley and Sons, Inc., NY, NY, pp. 16.0.5-16.22.17; Sigma-Aldrich, Co. (2001) *Products for Life Science Research*, St. Louis, Mo.; pp. 45-89; Amersham Pharmacia Biotech (2001) *BioDirectory*, Piscataway, N.J., pp. 384-391). Production, purification, and fragmentation of polyclonal and monoclonal antibodies are described (Coligan, et al. (2001) *Current Protocols in Immunology, Vol.* 1, John Wiley and Sons, Inc., New York; Harlow and Lane (1999) *Using Antibodies*, Cold Spring Harbor Laboratory Press, Cold Spring Harbor, N.Y.; Harlow and Lane, supra). Standard techniques for characterizing ligand/receptor interactions are available (see, e.g., Coligan, et al. (2001) *Current Protocols in Immunology*, Vol. 4, John Wiley, Inc., New York).

EXAMPLES

Example 1: Androstane- and Preganane-Derivative as an Efficacious and Specific G6PD Inhibitors G6PD deficiency is common in humans, and several point mutations have been found in this enzyme in different ethnic groups around the world. Epidemiological studies suggest that individuals who harbor a Mediterranean-type non-synonymous mutation [single nucleotide polymorphism in exon 6: dbSNP rs5030868] have 80% less G6PD activity as compared to normal individuals and are less likely to have cardiovascular diseases (Gupte (2008): Curr Opin Investig Drugs; 9:993-1000), including sickle cell anemia-associated PH.

Several compounds with approximately 10-fold improved potency in an enzyme assay were identified, and this improved activity translated to efficacy in a cellular assay. The steroid inhibition of G6PD has been substantially developed; the 3β-alcohol can be replaced with 3β-H-bond donors such as sulfamide, sulfonamide, urea, and carbamate. Improved potency was achieved by replacing the androstane nucleus with a pregnane nucleus, provided a ketone at C-20 is present. For pregnan-20-ones incorporation of a 21-hydroxyl group is often beneficial. The novel compounds generally have good physicochemical properties and in vitro DMPK parameters. From >40 derivatives prepared three derivatives (Formula VI, Formula VII, Formula VIII) had IC50 in 1-10 µM ranges to inhibit G6PD activity. Also, these drugs displayed >100-fold efficacy to inhibit G6PD activity in vitro and in vivo than dehydroepiandrosterone and epi-androsterone. These drugs also showed good cardiovascular activity over other derivatives. Any modifications in the body of the nucleus (shown with a circle) of these drugs dampened or eliminated their cardiovascular actions. These potent steroid inhibitors with potential therapeutic utility will be beneficial in inhibiting G6PD and ameliorating cardiovascular diseases.

Example 2: Synthesis of G6Pd Inhibitors

N-Ethyl-N'-[(3β,5α)-17-oxoandrostan-3-yl]urea
(Compound 7e)

To a stirred solution of (3β,5α)-3-aminoandrostan-17-one, cyclic 1,2-ethanediyl acetal 6 (350 mg, 1.05 mmol) in DCM (5 mL) at 20° C. under nitrogen was added ethyl isocyanate (112 mg, 1.57 mmol). The mixture was stirred overnight, and then DCM and water were added before the mixture was passed through a hydrophobic frit. The DCM phase was concentrated to give the intermediate ketal as a white solid (472 mg). The 17-ketal intermediate (472 mg) was deprotected in a similar manner to compound 7a (as described in Hamilton et al., Novel Steroid Inhibitors of Glucose 6-Phosphate Dehydrogenase; J. Med. Chem. 2012, 55:4431-4445) and the crude product chromatographed on silica (25 g SNAP, DCM/ethyl acetate gradient elution), affording the product 7e as a white solid (293 mg, 77%). 1H NMR (CDCl3): δ 0.82 (s, 3H), 0.86 (s, 3H), 1.14 (t, J=7.3 Hz, 3H), 2.38-2.50 (m, 1H), 3.20 (q, J=7.2 Hz, 2H), 3.46-3.59 (m, 1H), 4.35 (br s, 1H). 1H NMR (DMSO-d6): δ 0.78 (s, 6H), 0.96 (t, J=7.2 Hz, 3H), 2.32-2.44 (m, 1H), 2.92-3.03 (m, 2H), 3.22-3.37 (m, 1H), 5.58-5.65 (m, 1H). 13C NMR (CDCl3): δ 12.3, 13.8, 15.5, 20.4, 21.8, 28.3, 29.6, 30.8, 31.5, 35.1, 35.3, 35.6, 35.9, 36.2, 37.5, 45.5, 47.8, 49.7, 51.4, 54.4, 157.6, 221.4. LC-MS m/z 361.2 [M+1]+, 100% purity; m/z 359.2 [M−1]−, 100% purity. HRMS (ESI) m/z+[M+H]+ m/z calculated for $C_{22}H_{37}N_2O_2$: 361.2850. Found: 361.2851.

Synthesis of 7a ((3β,5α)-3-Aminoandrostan-17-one)

(3β,5α)-3-Aminoandrostan-17-one, cyclic 1,2-ethanediyl acetal 6 (100 mg, 0.30 mmol) was dissolved in acetone (1 mL), DCM (1 mL) and THF (4 mL). Then 2 M HCl (0.5 mL, 1 mmol) was added and the mixture stirred overnight. The reaction mixture was basified with 1 M NaOH. DCM was added and the mixture stirred before passing through a hydrophobic frit. The organic phase was concentrated and chromatographed on silica (10 g SNAP cartridge, DCM/MeOH gradient elution) to give the product 7a as a white solid (10 mg, 12%). $^1$H NMR (CDC3): δ 0.84 (s, 3H), 0.88 (s, 3H), 2.40-2.52 (m, 1H), 2.70-2.82 (m, 1H). $^{13}$C NMR (CDCl$_3$): δ 11.2, 12.7, 19.3, 20.7, 27.3, 29.8, 30.4, 31.0, 34.0, 34.6, 34.7, 34.8, 36.4, 37.6, 44.4, 46.7, 49.9, 50.4, 220.3. HRMS (ESI) m/z [M+H]$^+$ calcd for $C_{19}H_{32}NO$: 290.2479. Found: 290.2480 Hamilton et al., Novel Steroid Inhibitors of Glucose 6-Phosphate Dehydrogenase; J. Med. Chem. 2012, 55:4431-4445. Hitchin et al., A novel scalable and stereospecific synthesis of 3α- and 3β-amino-5α-androstan-17-ones and 3α- and 3β-amino-5α-pregnan-20-ones. Tetrahedron Lett., 2012, 53(23): 2868-2872.

N-[(3β,5α)-20-Oxopregnan-3-yl]methanesulfonamide (Compound 14f)

14f was prepared and purified in a similar manner to compound 7h, using (3β,5α)-3-aminopregnan-20-one, 20-cyclic 1,2-ethanediyl acetal 13 (390 mg, 1.08 mmol) and methane sulfonyl chloride (0.13 mL, 1.62 mmol). Evaporation of the solvent afforded the product 14f as a white solid (255 mg, 60%). 1H NMR (CDCl3): δ 0.62 (s, 3H), 0.81 (s, 3H), 2.13 (s, 3H), 2.50-2.58 (m, 1H), 3.00 (s, 3H), 3.25-3.38 (m, 1H). 13C NMR (CDCl3): δ 12.2, 13.5, 21.2, 22.8, 24.4, 28.4, 30.3, 31.6, 31.8, 35.3, 35.4, 36.7, 37.4, 39.0, 42.3, 44.2, 45.5, 53.5, 54.1, 56.6, 63.8, 209.7. LC-MS m/z 394.1 [M−H]−, 100% purity. HRMS (ESI) m/z [M+Cl]− calcd for $C_{22}H_{37}ClNO_3S$: 430.2188. Found: 430.2201.

(3β,5α)-3,21-Dihydroxypregnan-20-one; Compound 34

To a stirred solution of (3β,5α)-21-bromo-3-hydroxypregnan-20-one 37 (1192 mg, 3 mmol) in DMF (100 mL) and water (50 mL) was added sodium hydroxide (144 mg, 3.6 mmol) and the mixture stirred for 30 min. The mixture was then diluted with water and extracted with ethyl acetate. The combined extracts were washed with water, dried, and the solvent evaporated. The residue was chromatographed on silica (isohexane/ethyl acetate gradient elution) and recrystallized from diethyl ether affording the product 34 as a white solid (761 mg, 76%); 1H NMR (CDCl3): δ 0.65 (s, 3H), 0.83 (s, 3H), 2.15-2.30 (m, 1H), 2.42-2.50 (m, 1H), 3.27 (br s, 1H) 3.53-3.67 (m, 1H), 4.15, 4.23 (ABq, JAB=18.9 Hz, 2H); 1H NMR (DMSO-d6): δ 0.52 (s, 3H), 0.74 (s, 3H), 1.95-2.07 (m, 1H), 2.55 (m, 1H), 4.02 (d, J=5.8 Hz, 2H), 4.42 (d, J=4.8 Hz, 1H), 4.89 (t, J=5.8 Hz, 1H); 13C NMR (CDCl3): δ 12.3, 13.5, 21.2, 22.9, 24.5, 28.6, 31.5, 32.0, 35.5, 37.0, 38.1, 38.8, 44.8, 45.0, 54.2, 56.8, 59.4, 69.4, 71.2, 77.2, 210.4; HRMS (ESI) m/z [M+Cl]− Calcd for C21H34ClO3: 369.2201. Found: 369.2211.

Alternative methods to synthesize the compounds are as follows.

(3β)-3,21-Dihydroxypregn-5-en-20-one. PD2124 (Compound 34)

(3β)-21-(acetyloxy)-3-hydroxy-pregn-5-en-20-one, (0.4000 g, 1.07 mmol) was mixed with ethanol (40 mL) under a nitrogen atmosphere. 10% Pd on charcoal (25 mg) was added and the system degassed using nitrogen. The reaction was degassed and placed under a hydrogen atmosphere. The mixture was stirred overnight at ambient temperature. Water was added and the mixture passed through celite dampened with water. All volatiles were removed and the residue dissolved in diethyl ether, dried over magnesium sulphate, filtered and the solvents removed to give a white solid. The crude material was loaded onto silica using dichloromethane then purified using a 25 g Biotage SNAP cartridge—eluting with 0-100% Ethyl acetate/isohexane. Concentration of the clean fractions gave (3β)-21-(acetyloxy)-3-hydroxy-pregn-5-en-20-one (55 mg, 12%) as a white powder.

To a solution of (3β)-21-(acetyloxy)-3-hydroxy-pregn-5-en-20-one (500 mg, 1.33 mmol) in methanol (10 mL) and water (1 mL) was added potassium carbonate (184.52 mg, 1.33 mmol) and the mixture stirred at reflux for 30 min TLC (silica, EtOAc eluant) showed complete conversion of starting ester (Rf 0.7) to a more polar product (Rf 0.6). The reaction mixture was concentrated under reduced pressure, diluted with water and extracted with EtOAc. The combined extracts were washed with water, dried over anhydrous Na$_2$SO$_4$ and concentrated under reduced pressure. This afforded a solid that was recrystallised from EtOAc affording (3β)-21-(acetyloxy)-3-hydroxypregn-5-en-20-one (164 mg).

To a solution of (3β)-21-(acetyloxy)-3-hydroxypregn-5-en-20-one (500 mg, 1.34 mmol) in methanol (10 mL) and water (1 mL) was added potassium carbonate (185 mg, 1.34 mmol) and the mixture stirred at reflux for 30 min. The reaction mixture was concentrated, diluted with water and extracted with ethyl acetate. The combined extracts were washed with water, dried and the solvent evaporated. The solid was recrystallized from ethyl acetate affording the product as a white solid (164 mg, 37%); $^1$H NMR (CDCl$_3$): δ 0.67 (s, 3H), 1.02 (s, 3H), 2.43-2.52 (m, 1H), 3.48-3.60 (m, 1H), 4.17, 4.25 (ABq, JAB=19.0 Hz, 2H), 5.34-3.39 (m, 1H); $^{13}$C NMR (CDCl$_3$): δ 13.3, 19.4, 21.0, 22.9, 24.6, 31.6, 31.8, 31.9, 36.5, 37.2, 38.6, 42.2, 44.8, 49.9, 57.0, 59.2, 69.4, 71.7, 121.3, 140.8, 210.3.

N-Ethyl-N'-[(3β,5a)-17-oxoandrostan-3-yl]urea. PD2958 (Compound 7e)

(3α,5α)-3-Hydroxyandrostan-17-one, cyclic 1,2-ethanediyl acetal (8.17 g, 24.4 mmol), phthalimide (3.59 g, 24.4 mmol), and TPP (7.08 g, 25.6 mmol) were dissolved in THF (175 mL), and the solution was cooled to 5° C. using an ice bath. DIAD (5.3 mL, 26.8 mmol) was added slowly maintaining the temperature below 5° C. A white precipitate formed during the reaction. The mixture was stirred and warmed to ambient temperature overnight under a nitrogen atmosphere. All volatiles were evaporated and methanol (100 mL) was added and the mixture stirred for 30 min. The precipitate was filtered off and washed with methanol. The solid was dried under vacuum to give 2-[(3β,5α)-17-Oxoandrostan-3-yl, 17-cyclic 1,2-ethanediylacetal]-1H-isoindole-1,3(2H)-dione as a white solid (7.67 g, 68%). 1H NMR (CDCl3): δ 0.87 (s, 3H), 0.98 (s, 3H), 1.95-2.05 (m, 1H), 2.22-2.49 (m, 2H), 3.85-3.97 (m, 4H), 4.13-4.24 (m, 1H), 7.68-7.74 (m, 2H), 7.79-7.85 (m, 2H).

2-[(3β,5α)-17-Oxoandrostan-3-yl, 17-cyclic 1,2-ethanediylacetal]-1H-isoindole-1,3(2H)-dione (7.67 g, 15.6 mmol) was mixed with ethanol (100 mL) and hydrazine hydrate (11 mL, 226 mmol) and refluxed overnight under a nitrogen atmosphere. The reaction mixture was cooled, and the solid was filtered off. The filtrate was evaporated to dryness. The residue was partitioned between DCM and water, and the solution passed through a hydrophobic frit. The DCM phase was evaporated to dryness to give the (3β,5α)-3-aminoandrostan-17-one, cyclic 1,2-ethanediyl acetal (5.34 g, 97%). 1H NMR (CDCl3): δ 0.79 (s, 3H), 0.84 (s, 3H), 1.92-2.04 (m, 1H), 2.61-2.73 (m, 1H), 3.82-3.98 (m, 4H).

To a stirred solution of (3β,5α)-3-aminoandrostan-17-one, cyclic 1,2-ethanediyl acetal (350 mg, 1.05 mmol) in DCM (5 mL) at 20° C. under nitrogen was added ethyl isocyanate (112 mg, 1.57 mmol). The mixture was stirred overnight, and then DCM and water were added before the mixture was passed through a hydrophobic frit. The DCM phase was concentrated to give the intermediate ketal as a white solid (472 mg). The 17-ketal intermediate (472 mg) was dissolved in acetone (1 mL), DCM (1 mL) and THF (4 mL), 2 M HCl (0.5 mL, 1 mmol) was added and the mixture stirred overnight. The reaction mixture was basified with 1 M NaOH. DCM was added and the mixture stirred before passing through a hydrophobic frit. The organic phase was concentrated and chromatographed on silica (25 g SNAP, DCM/ethyl acetate gradient elution), affording N-Ethyl-N'-[(3β,5α)-17-oxoandrostan-3-yl]urea as a white solid (293 mg, 77%). $^1$H NMR (CDCl$_3$): δ 0.82 (s, 3H), 0.86 (s, 3H), 1.14 (t, J=7.3 Hz, 3H), 2.38-2.50 (m, 1H), 3.20 (q, J=7.2 Hz, 2H), 3.46-3.59 (m, 1H), 4.35 (br s, 1H). 1H NMR (DMSO-d6): δ 0.78 (s, 6H), 0.96 (t, J=7.2 Hz, 3H), 2.32-2.44 (m, 1H), 2.92-3.03 (m, 2H), 3.22-3.37 (m, 1H), 5.58-5.65 (m, 1H). $^{13}$C NMR (CDCl$_3$): δ 12.3, 13.8, 15.5, 20.4, 21.8, 28.3, 29.6, 30.8, 31.5, 35.1, 35.3, 35.6, 35.9, 36.2, 37.5, 45.5, 47.8, 49.7, 51.4, 54.4, 157.6, 221.4. LC-MS m/z 361.2 [M+H]+, 100% purity; m/z 359.2 [M−H]−, 100% purity. HRMS (ESI) m/z [M+H]+ m/z calcd for C22H37N2O2: 361.2850. Found: 361.2851.

N-[(3β,5α)-17-Oxoandrostan-3-yl]sulfamide. PD4091 (Compound 14f)

(3β,5α)-3-Hydroxyandrostan-17-one, cyclic 1,2-ethanediyl acetal (5.83 g, 17.4 mmol), phthalimide (2.56 g, 17.4 mmol), and TPP (5.06 g, 18.3 mmol) were dissolved in THF (140 mL) and cooled to 5° C. using an ice bath. DIAD (3.8 mL, 19.2 mmol) was added slowly, maintaining the temperature below 7° C. The yellow color was allowed to disappear between additions. The mixture was allowed to warm to ambient temperature overnight under a nitrogen atmosphere. The solvent was evaporated and methanol was added to the oil, forming a white precipitate. The suspension was stirred for 30 min. The precipitate was filtered off and washed with methanol (100 mL), affording 2-[(3β,5α)-17-Oxoandrostan-3-yl, 17-cyclic 1,2-ethanediyl acetal]-1H-isoindole-1,3(2H)-dione as a white solid (5.93 g, 74%). $^1$H NMR (CDCl$_3$): δ 0.77 (s, 3H), 0.78 (s, 3H), 3.75-3.86 (m, 4H), 4.41-4.42 (m, 1H), 7.60-7.65 (m, 2H), 7.71-7.77 (m, 2H).

2-[(3β,5α)-17-Oxoandrostan-3-yl, 17-cyclic 1,2-ethanediyl acetal]-1H-isoindole-1,3(2H)-dione (5.93 g, 12.8 mmol) was treated with ethanol (180 mL) and hydrazine hydrate (8.0 mL, 164 mmol) and the mixture heated at reflux overnight under a nitrogen atmosphere. The reaction mixture was cooled and the solid precipitate was filtered off. The filtrate was evaporated and the residue partitioned between DCM and water, and then passed through a hydrophobic frit. The DCM phase was evaporated to give 2-[(3β,5α)-17-Oxoandrostan-3-yl, 17-cyclic 1,2-ethanediyl acetal]-1H-isoindole-1,3(2H)-dione as a white solid (4.06 g, 95%); $^1$H NMR (CDCl$_3$): δ0.dos (s, 3H), 0.76 (s, 3H), 1.85-1.94 (m, 1H), 3.01-3.11 (br s, 1H), 3.75-3.87 (m, 4H).

A magnetically stirred solution of Sulfamide (481.26 mg, 5.01 mmol) and 2-[(3β,5α)-17-Oxoandrostan-3-yl, 17-cyclic 1,2-ethanediyl acetal]-1H-isoindole-1,3(2H)-dione (167. mg, 0.50 mmol) in 1,4-dioxane (5 mL) was heated at reflux with stirring for 48 h. The reaction mixture was diluted with water and extracted with ethyl acetate. The combined extracts were washed with saturated NaHCO3 and water. The organic phase was dried and evaporated to leave a residue which was treated with water (2 mL), MeOH (3 mL) and MeSO3H (0.4 mL) and stirred vigorously for 15 min. The reaction mixture was basified with saturated NaHCO3 (~10 mL) and passed through a hydrophobic filter. The aqueous phase was washed with DCM. The organic phase was concentrated to dryness affording residue which was chromatographed over silica (isohexane/EtOAc eluant) to give N-[(3β,5α)-17-Oxoandrostan-3-yl]sulfamide (115 mg, 51%) as an off-white powder. $^1$H NMR (DMSO-d6): δ 0.77 (s, 3H), 0.78 (s, 3H), 2.32-2.44 (m, 1H), 3.42-3.51 (m, 1H), 6.36 (br d, J=5.9 Hz, 1H), 6.40 (br s, 2H). $^{13}$C NMR (DMSO-d6): δ 11.4, 13.4, 19.6, 21.3, 26.2, 27.8, 30.5, 31.4, 31.9, 33.1, 34.4, 35.2, 35.4, 38.7, 47.1, 48.2, 50.8, 53.6, 219.8. LC-MS m/z 367.1 [M−1]−.

Experimental Methods

Flash chromatography was performed using pre-packed silica gel cartridges (KP-Sil SNAP, Biotage, Hengoed UK or RediSep Rf, Isco). Thin layer chromatography was conducted with 5×10 cm plates coated with Merck Type 60 F254 silica gel to a thickness of 0.25 mm. All reagents obtained from commercial sources were used without further purification. Anhydrous solvents were obtained from the Sigma-Aldrich Chemical Company Ltd. or Fisher Chemicals Ltd., and used without further drying. HPLC grade solvents were obtained from Fisher Chemicals Ltd.

All compounds were >90% purity as determined by examination of both the LC-MS and 1H NMR spectra unless otherwise indicated. Where Cl or Br were present, expected isotopic distribution patterns were observed.

$^1$H NMR

Proton ($^1$H) and carbon ($^{13}$C) NMR spectra were recorded on a 300 MHz Bruker spectrometer. Solutions were typically prepared in either deuterochloroform (CDCl$_3$) or deuterated dimethylsulfoxide (d6-DMSO) with chemical shifts referenced to tetramethylsilane (TMS) or deuterated solvent as an internal standard. $^1$H NMR data are reported indicating the chemical shift (δ), the integration (e.g. 1H), the multiplicity (s, singlet; d, doublet; t, triplet; q, quartet; m, multiplet; br, broad; dd, doublet of doublets etc.) and the coupling constant (J) in Hz (app implies apparent coupling on broadened signals). Deuterated solvents were obtained from the Sigma-Aldrich Chemical Company, Goss or Fluorochem.

Analytical LC-MS.

LC-MS analyses were performed on a Waters Acquity UPLC system fitted with BEH C18 1.7 μm columns (1.1×50 mm) and with UV diode array detection (210-400 nm). Positive and negative mass ion detection was performed using a Waters SQD detector. Analyses were performed with either buffered acidic or basic solvents and gradients as detailed below:

Low pH:
  Solvent A—Water+10 mM ammonium formate+0.1% formic acid
  Solvent B—Acetonitrile+5% water+0.1% formic acid
High pH:
  Solvent A—Water+10 mM ammonium hydrogen carbonate+0.1% ammonia solution Solvent B—Acetonitrile+0.1% ammonia solution
Gradient:

| Time | Flow rate (mL/min) | % Solvent A | % Solvent B |
|------|--------------------|-------------|-------------|
| 0    | 0.6                | 95          | 5           |
| 1.2  | 0.6                | 5           | 95          |
| 1.7  | 0.6                | 5           | 95          |
| 1.8  | 0.6                | 95          | 5           |

Example 3

Mice were exposed to hypoxia (10% O2) or to ambient atmosphere (21% O2) for 5 weeks. These mice developed pulmonary hypertension (PH group). Mice were treated with PD2124 (Compound 34) s.c. for 1 week. Body weight and hematocrit was measured (FIG. 2).

Figure 3B:
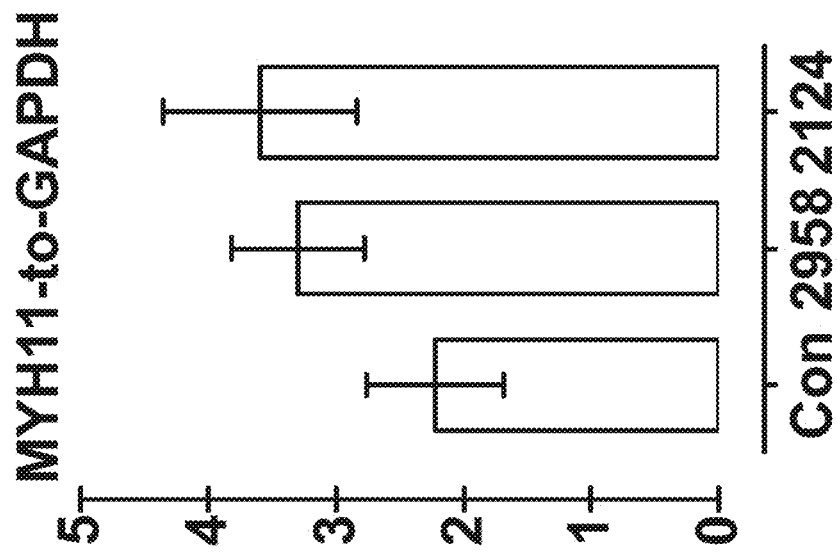
FIGS. 3A and 3B are graphs showing results for bovine pulmonary arteries that were incubated in Krebs buffer with and without G6PD inhibitor PD2958 (2958) and PD2124 (2124) for 12 hr. Vascular smooth cell-specific protein myocardin (MYOCD.
Figure 3A:
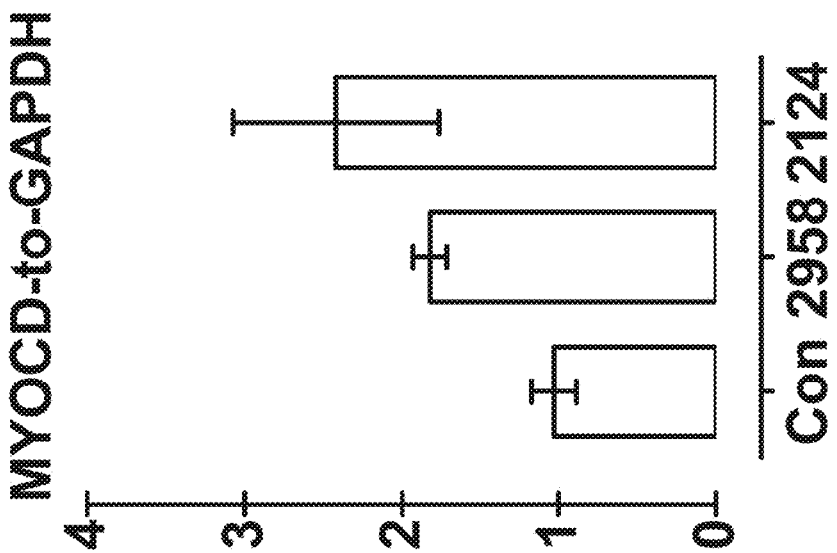

Bovine pulmonary arteries were incubated in Krebs buffer with and without G6PD inhibitor PD2958 (2958) and PD2124 (2124) for 12 hr. Vascular smooth cell-specific protein myocardin (MYOCD) and smooth muscle myosin heavy chain (MHY11) expression was increased by PD2958 (10 microM) and PD2124 (1 microM) (FIGS. 3A and 3B).

Figure 4B:
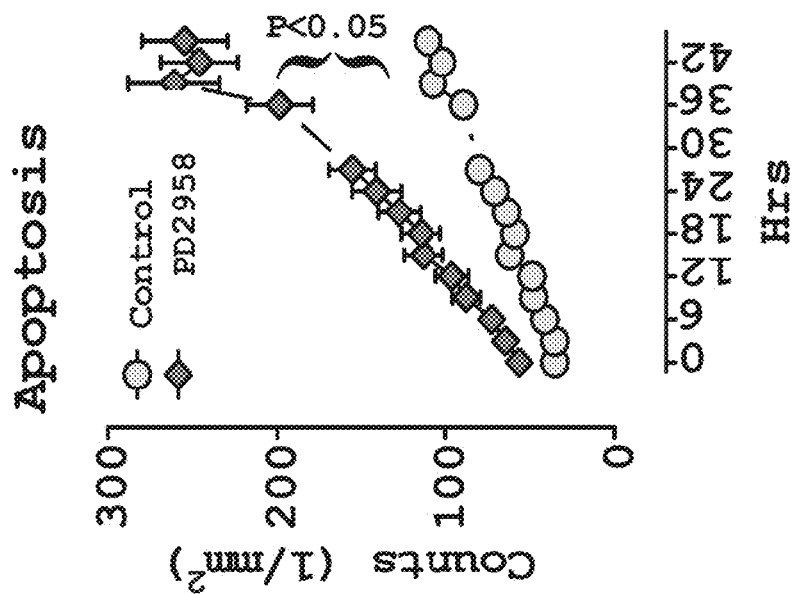
FIGS. 4A and 4B are graphs showing results for rat pulmonary artery smooth muscle cells that were cultured in 15% DMEM media for 48 hr and cells were treated with newly synthesized G6PD drugs; PD109 (109), PD2124 (2124), PD2958 (2958) and PD4091 (4091) or vehicle control (Con) for 72 hr. Cell number/proliferation (FIG. 4A) and apoptosis (FIG. 4B) was determined by Cyquant and Caspase3/7 assay, respectively. Cell numbers were decreased by G6PD inhibitors (FIG. 4A). Cell apoptosis was increased by PD2958 (1 microM) N=5 in each group (FIG. 4B).
Figure 4A:
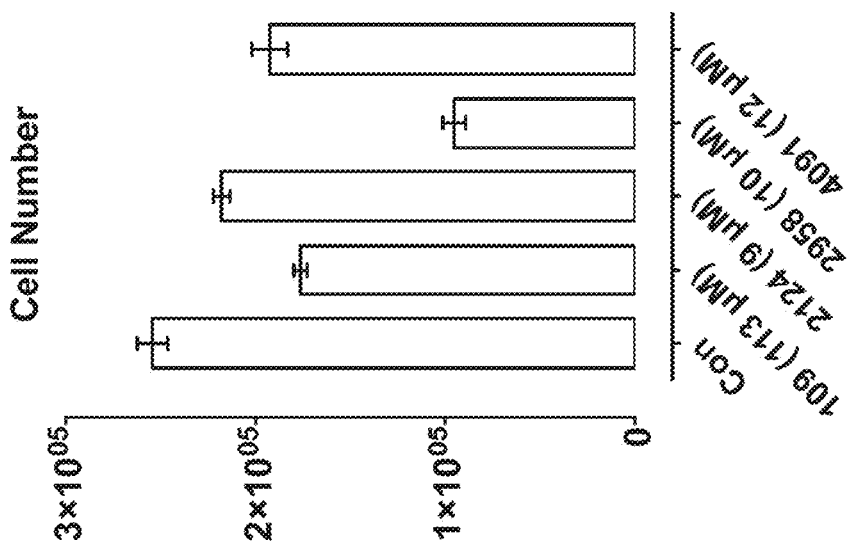

Rat pulmonary artery smooth muscle cells were cultured in 15% DMEM media for 48 hr and cells were treated with newly synthesized G6PD drugs; PD109 (109), PD2124 (2124), PD2958 (2958) and PD4091 (4091) or vehicle control (Con) for 72 hr. Cell number/proliferation and apoptosis was determined by Cyquant and Caspase3/7 assay, respectively. Cell numbers were decreased by G6PD inhibitors. Cell apoptosis was increased by PD2958 (1 microM) N=5 in each group (FIGS. 4A and 4B).

Figure 5B:
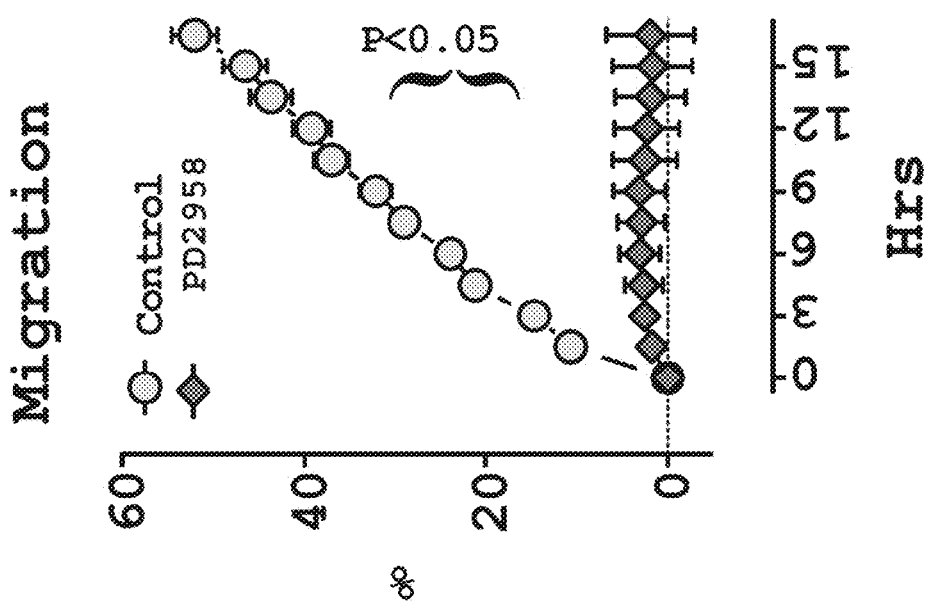
FIGS. 5A and 5B are images (FIG. 5A) and a graph (FIG. 5B) showing rat pulmonary artery smooth muscle cells that were cultured in 15% DMEM media for 48 hr and cells were treated with newly synthesized G6PD drugs; PD2958 (2958) or vehicle control (Con) for 72 hr. Cells migration was determined. Cell migration was abrogated by PD2958 (1 microM). N=5 in each group.
Figure 5A:
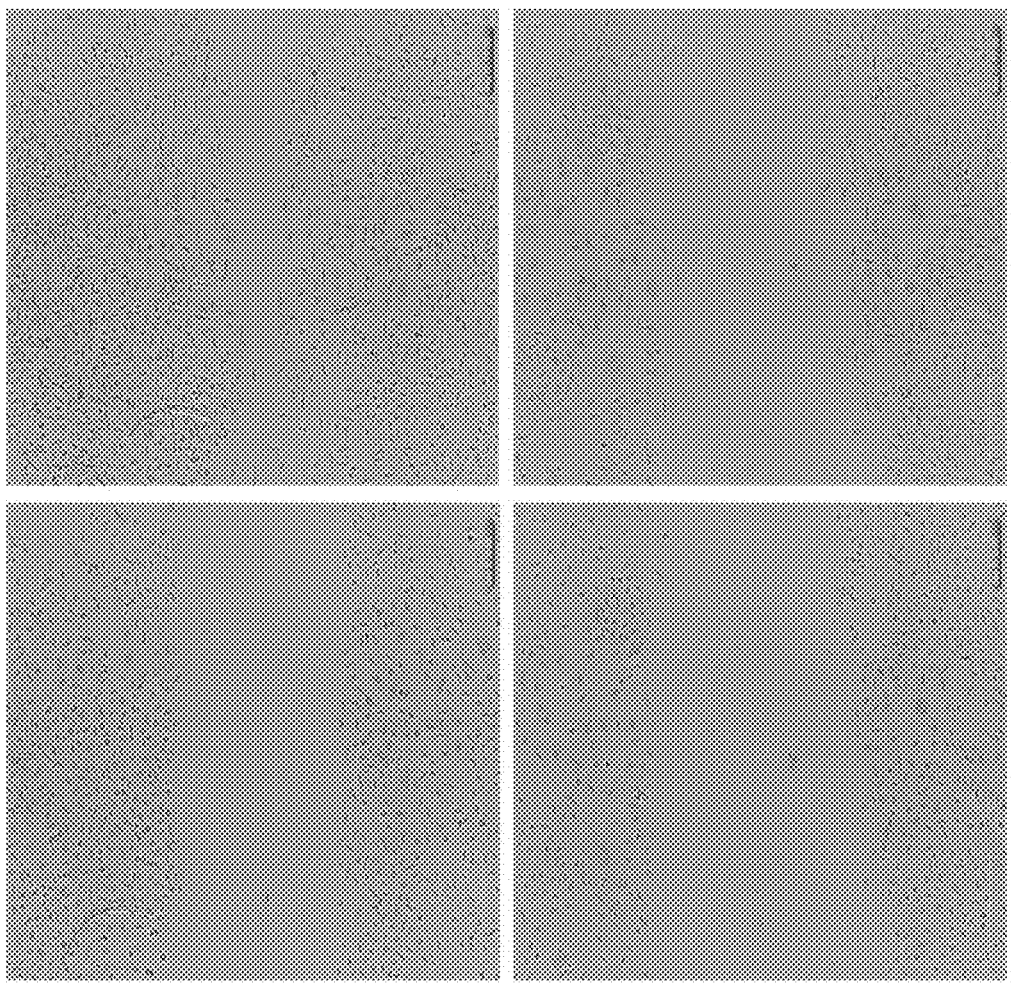

Rat pulmonary artery smooth muscle cells were cultured in 15% DMEM media for 48 hr and cells were treated with newly synthesized G6PD drugs; PD2958 (2958) or vehicle control (Con) for 72 hr. Cells migration was determined. Cell migration was abrogated by PD2958 (1 microM). N=5 in each group (FIGS. 5A and 5B).

Figure 6:
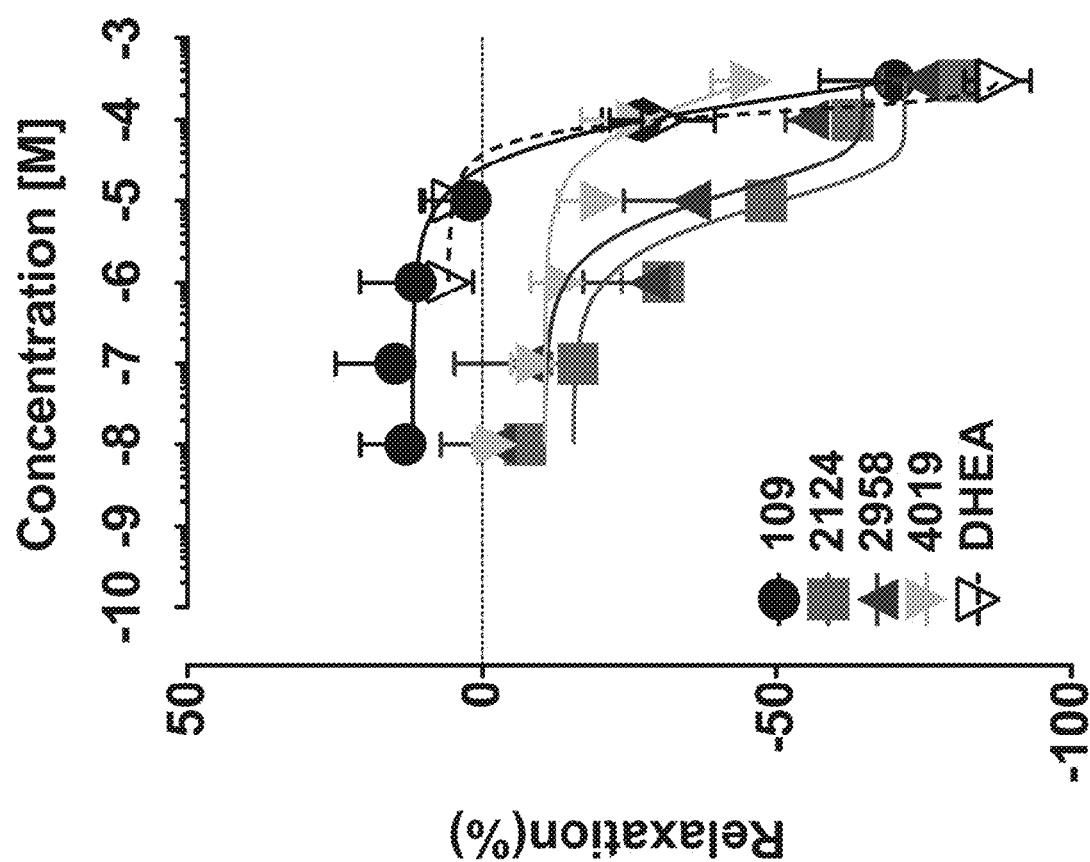
FIG. 6 is a graph showing bovine pulmonary artery rings that were incubated in Krebs buffer and pre-contracted with KCl (30 mM). These pre-contracted rings relaxed by G6PD inhibitors; PD109 (109), PD2124 (2124), PD2958 (2958) and PD4091 (4091) or dehydroepiandrosterone (DHEA).

Bovine pulmonary artery rings were incubated in Krebs buffer and pre-contracted with KCl (30 mM). These pre-contracted rings relaxed by G6PD inhibitors; PD109 (109), PD2124 (2124), PD2958 (2958) and PD4091 (4091) or dehydroepiandrosterone (DHEA) (FIG. 6).

Figure 7:
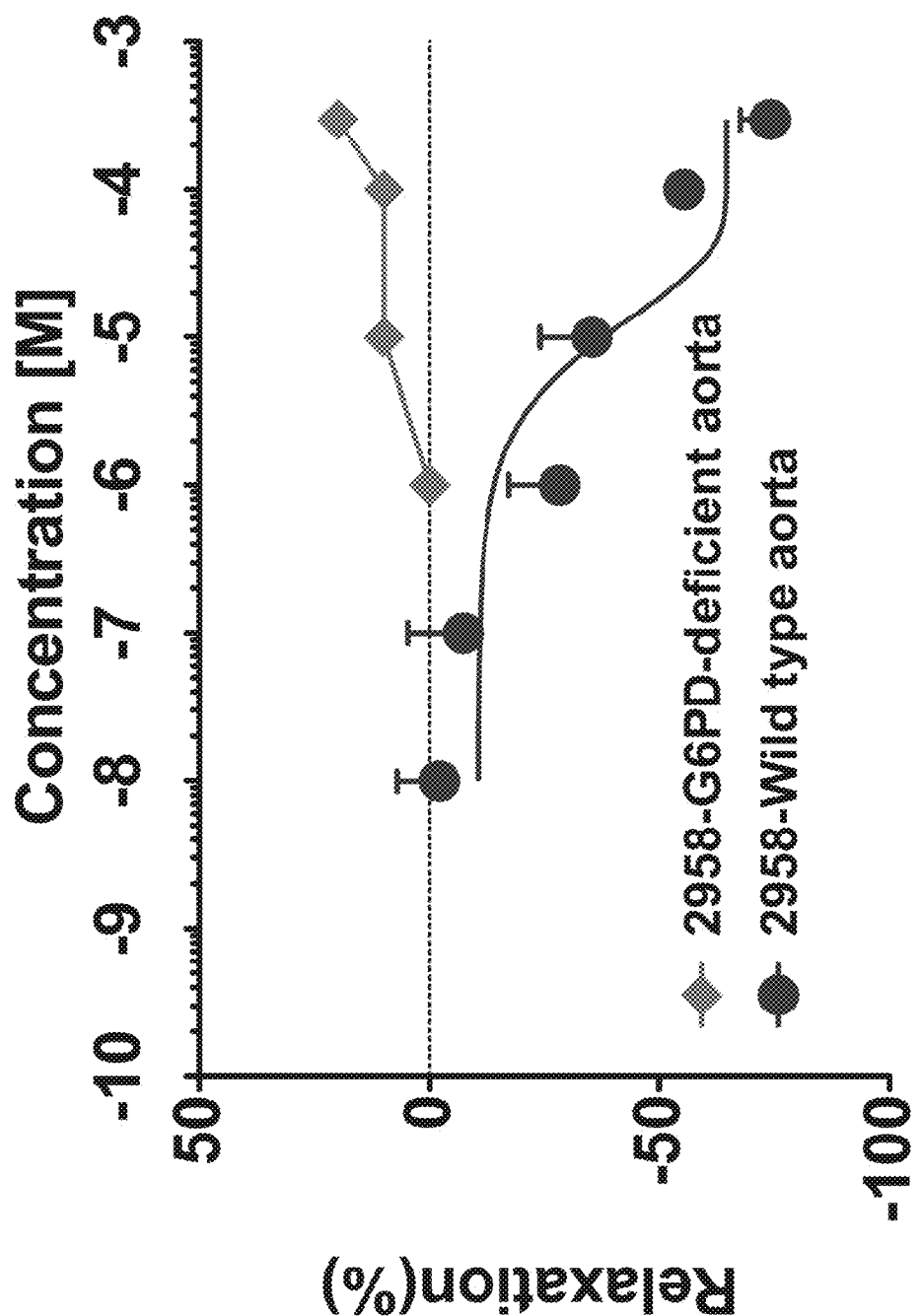
FIG. 7 is a graph showing aortic rings of wild-type and G6PD-deficient pre-contracted with KCl (30 mM). These rings from wild-type but not G6PD-deficient mice were relaxed in dose-dependent manner by PD2958 (2958).

Aortic rings of wild-type and G6PD-deficient pre-contracted with KCl (30 mM). These rings from wild-type but not G6PD-deficient mice were relaxed in dose-dependent manner by PD2958 (2958) (FIG. 7).

Mice were divided in four groups; control (ctrl) exposed to ambient atmosphere (21% 02); pulmonary hypertension exposed to 10% O$_2$ (PH); PH treated with inactive G6PD inhibitor (PH_Placebo); and PH treated with active G6PD inhibitor (PH_2124) for 5 wk. Placebo and 2124 were injected S.C. (1.3 mg/Kg) for 1 wk from wk 4 to wk 5. G6PD inhibitor 2124 reduced and reversed pulmonary resistance determined as PAAT-to-ET ratio, arterial elastance, and TPR (FIGS. 8A-8C).

Figure 9B:
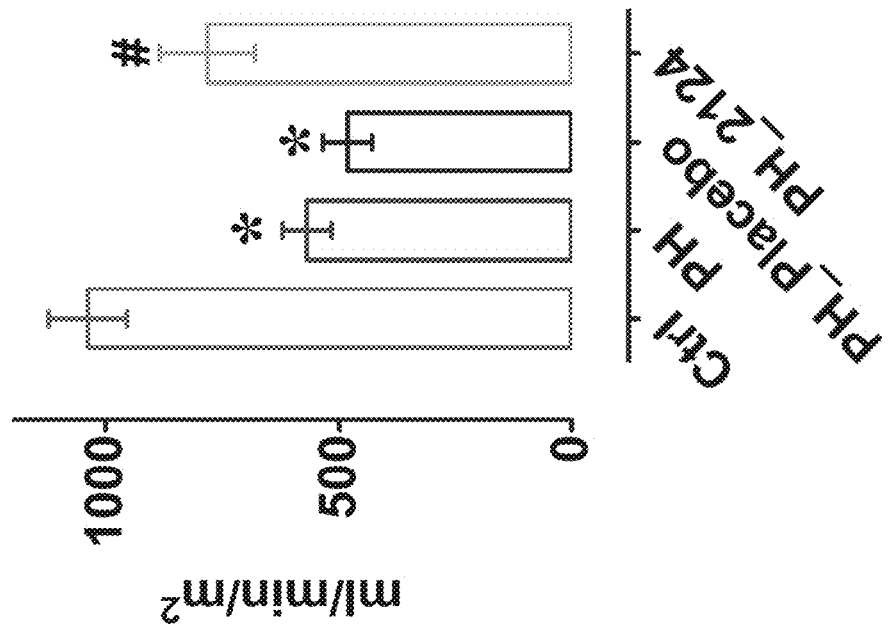
FIGS. 9A and 9B are graphs showing results for mice that were divided in four groups and treated under the following conditions: control (ctrl) exposed to ambient atmosphere (21% $O_2$); pulmonary hypertension exposed to 10% $O_2$ (PH); PH treated with inactive G6PD inhibitor (PH_Placebo); and PH treated with active G6PD inhibitor (PH_2124) for 5 wk. Placebo and 2124 were injected S.C. (1.3 mg/Kg) for 1 wk from wk 4 to wk 5. G6PD inhibitor 2124 reduced and reversed left ventricle (LV) stiffness (FIG. 9A) and increased cardiac index (FIG. 9B).
Figure 9A:
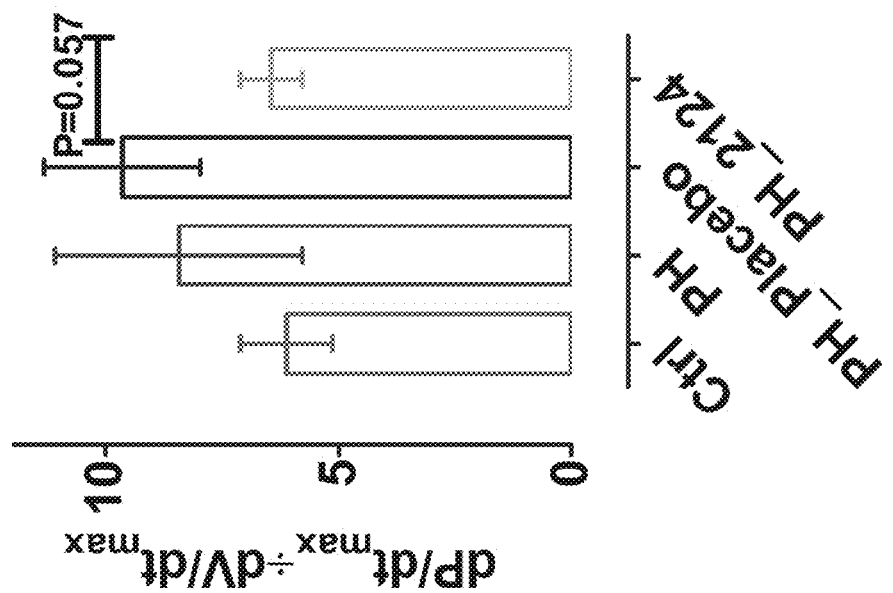

Mice were divided in four groups; control (ctrl) exposed to ambient atmosphere (21% O2); pulmonary hypertension exposed to 10% O2 (PH); PH treated with inactive G6PD inhibitor (PH_Placebo); and PH treated with active G6PD inhibitor (PH_2124) for 5 wk. Placebo and 2124 were injected S.C. (1.3 mg/Kg) for 1 wk from wk 4 to wk 5. G6PD inhibitor 2124 reduced and reversed left ventricle (LV) stiffness and increased cardiac index (FIGS. 9A-9B).

Many modifications and variations of this invention can be made without departing from its spirit and scope, as will be apparent to those skilled in the art. The invention is defined by the terms of the appended claims, along with the full scope of equivalents to which such claims are entitled. The specific embodiments described herein, including the following examples, are offered by way of example only, and do not by their details limit the scope of the invention.

All references cited herein are incorporated by reference to the same extent as if each individual publication, database entry (e.g. Genbank sequences or GeneID entries), patent application, or patent, was specifically and individually indicated to be incorporated by reference. This statement of incorporation by reference is intended by Applicants, pursuant to 37 C.F.R. § 1.57(b)(1), to relate to each and every individual publication, database entry (e.g. Genbank sequences or GeneID entries), patent application, or patent, each of which is clearly identified in compliance with 37 C.F.R. § 1.57(b)(2), even if such citation is not immediately adjacent to a dedicated statement of incorporation by reference. The inclusion of dedicated statements of incorporation by reference, if any, within the specification does not in any way weaken this general statement of incorporation by reference. Citation of the references herein is not intended as an admission that the reference is pertinent prior art, nor does it constitute any admission as to the contents or date of these publications or documents.

The present invention is not to be limited in scope by the specific embodiments described herein. Indeed, various modifications of the invention in addition to those described herein will become apparent to those skilled in the art from the foregoing description and the accompanying figures. Such modifications are intended to fall within the scope of the appended claims.

The foregoing written specification is considered to be sufficient to enable one skilled in the art to practice the invention. Various modifications of the invention in addition to those shown and described herein will become apparent to those skilled in the art from the foregoing description and fall within the scope of the appended claims.

What is claimed is:

1. A method for treating a cardiovascular disorder and/or a pulmonary disorder in a subject in need thereof, comprising administering to the subject a therapeutically effective amount of a compound comprising N-((3β, 5α)-20-Oxopregnan-3-yl) methanesulfonamide, N-ethyl-N'-((3β, 5α)-17-oxoandrostan-3-yl)urea, (3β,5a)-3,21-Dihydroxypregnan-20-one, or N-((3β,5α)-17-Oxoandrostan-3yl)sulfamide or any combination thereof, or a pharmaceutically acceptable salt (crystal and/or amorphous), non-salt amorphous form, solvate, poly-morph, tautomer or prodrug thereof, wherein the cardiovascular disorder and/or pulmonary disorder comprises pulmonary hypertension, hypertension, medial hypertrophy, or combinations thereof, and wherein the therapeutically effective amount of the compound is between 10 to 300 mg/day.

2. The method of claim 1, wherein the cardiovascular disorder and/or pulmonary disorder comprises any of pulmonary hypertension groups 1, 3, 4 and 5, or combinations thereof.

3. The method of claim 2, wherein the cardiovascular disorder and/or pulmonary disorder comprises scleroderma, categorized as pulmonary hypertension group I.

4. The method of claim 1, wherein the therapeutically effective amount of the compound is between 30 to 200 mg/day.

* * * * *